United States Patent
Hafenrichter et al.

(10) Patent No.: US 9,643,313 B2
(45) Date of Patent: May 9, 2017

(54) APPARATUS FOR AUTOMATED MAINTENANCE OF AIRCRAFT STRUCTURAL ELEMENTS

(71) Applicant: The Boeing Company, Chicago, IL (US)

(72) Inventors: Joseph L. Hafenrichter, Seattle, WA (US); Gary E. Georgeson, Tacoma, WA (US); Scott W. Lea, Renton, WA (US)

(73) Assignee: The Boeing Company, Chicago, IL (US)

( * ) Notice: Subject to any disclaimer, the term of this patent is extended or adjusted under 35 U.S.C. 154(b) by 1170 days.

(21) Appl. No.: 13/663,709

(22) Filed: Oct. 30, 2012

(65) Prior Publication Data

US 2013/0289766 A1  Oct. 31, 2013

Related U.S. Application Data

(63) Continuation-in-part of application No. 12/657,424, filed on Jan. 19, 2010, now Pat. No. 8,347,746.

(51) Int. Cl.
*B25J 5/00* (2006.01)
*B25J 9/02* (2006.01)
(Continued)

(52) U.S. Cl.
CPC . *B25J 9/02* (2013.01); *B25J 5/00* (2013.01); *B64F 5/0045* (2013.01); *F01D 5/005* (2013.01);
(Continued)

(58) Field of Classification Search
CPC ..... B25J 5/00; B25J 9/02; B25J 11/005; B25J 11/008; Y10S 901/01
(Continued)

(56) References Cited

U.S. PATENT DOCUMENTS 4,146,967 A * 4/1979 Rohner ............... G01B 5/0002
33/530
5,031,458 A * 7/1991 Young ................. G01N 29/265
73/618
(Continued)

FOREIGN PATENT DOCUMENTS

EP  2345881 A1  7/2011

OTHER PUBLICATIONS

Extended European Search Report for European Application No. 13182082.1 (European counterpart of the instant U.S. Appl. No.) dated Feb. 24, 2016.
(Continued)

*Primary Examiner* — Peter Macchiarolo
*Assistant Examiner* — Alexander Mercado
(74) *Attorney, Agent, or Firm* — Ostrager Chong Flaherty & Broitman P.C.

(57) ABSTRACT

Automated apparatus for performing maintenance functions on airfoil-shaped bodies having short chord lengths, the apparatus being movable in a spanwise direction along the airfoil-shaped body. In accordance with various embodiments, the apparatus comprises a blade crawler capable of supporting any one of a plurality of end effectors for performing a set of maintenance functions on an airfoil-shaped body, such as a blade component. Included in these functions are multiple options for nondestructive inspection, drilling, grinding, fastening, appliqué application, scarfing, ply mapping, depainting, cleaning, and painting devices that are attached as the end effector for the blade crawler. As a whole, the blade crawler reduces maintenance time, labor hours and human errors when robotic maintenance functions are performed on blade components.

15 Claims, 13 Drawing Sheets

(51) Int. Cl.
*F01D 5/00* (2006.01)
*G01M 5/00* (2006.01)
*G01N 29/04* (2006.01)
*G01N 29/22* (2006.01)
*G01N 29/265* (2006.01)
*G01N 27/90* (2006.01)
*G01N 29/28* (2006.01)
*G01L 11/02* (2006.01)
*B64F 5/00* (2017.01)
*B25J 11/00* (2006.01)

(52) U.S. Cl.
CPC ......... *G01L 11/025* (2013.01); *G01M 5/0016* (2013.01); *G01M 5/0075* (2013.01); *G01N 27/90* (2013.01); *G01N 29/043* (2013.01); *G01N 29/225* (2013.01); *G01N 29/265* (2013.01); *G01N 29/28* (2013.01); *B25J 11/005* (2013.01); *B25J 11/008* (2013.01); *G01N 2291/0422* (2013.01); *G01N 2291/106* (2013.01); *G01N 2291/2694* (2013.01); *Y02T 50/672* (2013.01); *Y10S 901/01* (2013.01)

(58) Field of Classification Search
USPC ............... 73/618, 640, 866.5, 865.8; 904/44
See application file for complete search history.

(56) References Cited

U.S. PATENT DOCUMENTS

| | | | | |
|---|---|---|---|---|
| 5,623,107 A * | 4/1997 | Patterson, Sr. | .... | G01N 29/0645 73/865.8 |
| 5,698,787 A * | 12/1997 | Parzuchowski | .... | G01N 29/2418 73/583 |
| 6,167,760 B1 * | 1/2001 | Brunty | ............... | G01N 29/0645 73/634 |
| 6,220,099 B1 * | 4/2001 | Marti | ................... | G01N 29/226 73/633 |
| 6,378,387 B1 * | 4/2002 | Froom | ................ | G01M 5/0016 73/865.8 |
| 6,829,959 B2 | 12/2004 | Gifford et al. | | |
| 7,231,826 B2 | 6/2007 | Bossi et al. | | |
| 7,240,556 B2 | 7/2007 | Georgeson et al. | | |
| 7,315,609 B2 | 1/2008 | Safai et al. | | |
| 7,337,673 B2 | 3/2008 | Kennedy et al. | | |
| 7,562,593 B2 | 7/2009 | Engelbart et al. | | |
| 7,626,383 B1 * | 12/2009 | Sun | ........................ | G01N 27/82 324/232 |
| 7,640,811 B2 | 1/2010 | Kennedy et al. | | |
| 7,716,989 B2 * | 5/2010 | Kollgaard | ............. | G01N 27/90 73/627 |
| 8,483,356 B2 * | 7/2013 | Bendahan | ........... | G01V 5/0025 378/197 |
| 8,743,196 B2 * | 6/2014 | Fritz | ....................... | F03D 1/003 348/92 |
| 9,250,213 B1 * | 2/2016 | Bossi | ................... | G01N 29/265 |
| 9,334,066 B2 * | 5/2016 | Tapia | ................... | B64F 5/0045 |
| 2002/0036108 A1 * | 3/2002 | Jeswine | ............. | B62D 49/0621 180/164 |
| 2003/0147493 A1 * | 8/2003 | Bueno | .................... | G01N 23/04 378/57 |
| 2006/0043303 A1 | 3/2006 | Safai et al. | | |
| 2007/0096727 A1 * | 5/2007 | Rempt | ................. | G01N 27/904 324/238 |
| 2009/0038398 A1 | 2/2009 | Lavoie et al. | | |
| 2010/0011864 A1 * | 1/2010 | Hanan | ................. | G01N 29/265 73/620 |
| 2011/0178727 A1 * | 7/2011 | Hafenrichter | ....... | G01M 5/0016 702/38 |
| 2012/0060611 A1 * | 3/2012 | Thommen-Stamenkov | | F01D 21/003 73/632 |
| 2012/0153032 A1 * | 6/2012 | Svanebjerg | .......... | B64F 5/0063 239/1 |
| 2013/0261876 A1 * | 10/2013 | Froom | ................. | B64F 5/0045 701/29.3 |
| 2013/0289766 A1 * | 10/2013 | Hafenrichter | .............. | B25J 9/02 700/245 |
| 2013/0298682 A1 * | 11/2013 | Motzer | ................ | G01N 29/221 73/618 |
| 2013/0304251 A1 * | 11/2013 | Garvey | ................ | G01N 29/225 700/213 |
| 2014/0182479 A1 * | 7/2014 | Hafenrichter | ......... | B64F 5/0045 105/30 |
| 2014/0305216 A1 * | 10/2014 | Hafenrichter | .......... | G01N 29/07 73/598 |
| 2014/0365061 A1 * | 12/2014 | Vasquez | ................ | G05D 1/021 701/23 |

OTHER PUBLICATIONS

European Search Report for European Application No. 11151274.5; May 31, 2011; 4 pages.

MAUS Overview; http://www.boeing.com/defense-space/support/maintenance/commercial/maus.html; 4 pages.

* cited by examiner

Section A-A

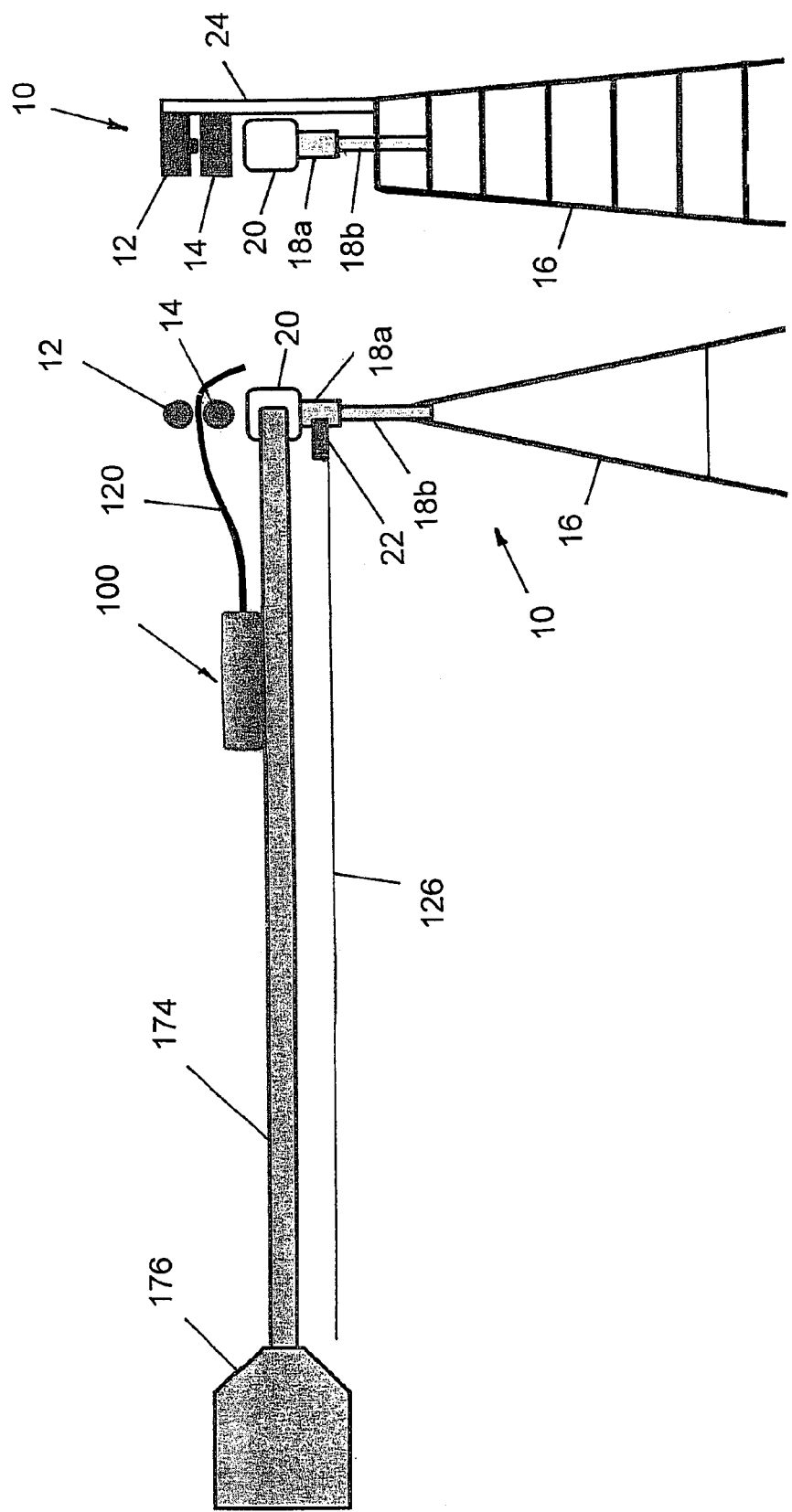

APPARATUS FOR AUTOMATED MAINTENANCE OF AIRCRAFT STRUCTURAL ELEMENTS

RELATED PATENT APPLICATION

This application is a continuation-in-part of and claims priority from U.S. patent application Ser. No. 12/657,424 filed on Jan. 19, 2010.

BACKGROUND

The present disclosure relates generally to the field of automated maintenance (including nondestructive inspection) of aircraft structural elements such as airfoil-shaped bodies, and more particularly to an automated end effector-carrying apparatus that is coupled to and travels along an airfoil-shaped body having a relatively short chord length, such as a rotorcraft blade, an aircraft propeller blade, a winglet, a projectile fin, an aircraft horizontal stabilizer, etc., while performing a maintenance function. As used herein, the term "maintenance" includes, but is not limited to, operations such as nondestructive inspection, drilling, scarfing, grinding (e.g., to remove bonded or bolted components), fastening, appliqué application, ply mapping, depainting, cleaning and painting.

In order to provide maintenance for airfoil-shaped bodies such as blade components, it is known to manually remove the blade components from the aircraft and then manually perform the maintenance functions. Removal of blade components from an aircraft is cost intensive. With helicopter blades, for example, the time spent removing, transporting, re-attaching, balancing and trimming the blades can be significant. Some helicopters require that the blades be removed and inspected every 50-75 flight hours, resulting in a dramatically reduced mission capability of the aircraft.

Furthermore, performing maintenance functions manually requires skilled technicians. These technicians are in short supply; therefore the labor cost to manually perform maintenance functions is significant.

Because manual maintenance is complex and repetitive, the likelihood of human error is high. When a repetitive maintenance operation is botched by a human, the flawed blade component could be reattached to the aircraft with a dangerous flaw still imbedded in the component. An aircraft accident could result from the blade component failing at the point of the flaw that could have been avoided with the use of a robot.

It would be desirable to have an automated apparatus for performing maintenance functions on airfoil-shaped bodies having short chord lengths, without the necessity of removing the airfoil-shaped body from the aircraft.

SUMMARY

The subject matter disclosed herein is an automated apparatus for performing maintenance functions on airfoil-shaped bodies having short chord lengths, without the necessity of removing the airfoil-shaped body from the aircraft. In accordance with various embodiments, the apparatus comprises a platform, an end effector selected from a group of interchangeable end effectors and carried by the platform, means for mounting the end effector-carrying platform on an airfoil-shaped body, means for moving the end effector-carrying platform in a spanwise direction along the airfoil-shaped body, and means for moving the end effector in a chordwise direction relative to the airfoil-shaped body when the platform is stationary.

In accordance with one embodiment, the apparatus comprises a blade crawler capable of supporting any one of a plurality of end effectors for performing a set of maintenance functions on an airfoil-shaped body such as a blade component. Included in these maintenance functions are multiple options for nondestructive inspection, drilling, grinding, fastening, appliqué application, scarfing, ply mapping, depainting, cleaning, and painting devices that are attached as the end effector for the blade crawler. The blade crawler is movable in a spanwise direction and comprises a traveling element (e.g., a slider) that is linearly translatable in a chordwise direction when the spanwise-movable blade crawler is stationary. A selected one of a plurality of end effectors can be attached to the traveling element. In accordance with each maintenance operation, the selected end effector can be moved in a chordwise direction when the blade crawler is not moving in the spanwise direction. There are a number of types of blade components on aircraft that will benefit from maintenance automation, including helicopter blades, propeller blades, flaps, ailerons, trim tabs, slats, stabilators and stabilizers. As a whole, the blade crawler reduces maintenance time, labor hours and human errors when robotic maintenance functions are performed on blade components.

To facilitate the mounting and removal of the automated blade crawler disclosed herein and prevent damage to the rotorcraft blade due to the weight of the crawler, an adjustable blade tip stabilizing apparatus is provided for supporting the tip of a rotorcraft blade during inspection or maintenance. This feature enables the crawler to function on smaller or less stiff rotorcraft blades without overloading them. The blade tip stabilizing apparatus further comprises a cable payout subsystem for managing the cables which connect the crawler to the operations center.

The disclosed blade crawler and blade stabilizer will enable on-aircraft maintenance operations. This means that the blade component will not need to be removed from the aircraft, and the functions of removing, transporting, re-attaching, balancing and trimming need not be performed, resulting in a dramatically increased mission capability of the aircraft. In addition, performing maintenance functions robotically with a blade crawler will reduce the workload on the limited number of skilled technicians, thus reducing the labor cost to perform maintenance functions. Also, human error will be dramatically reduced with the blade crawler performing the complex repetitive maintenance processes on blade components. Fewer aircraft accident will result from the blade component failing because fewer flaws will be passed to the aircraft because a robot was employed.

One aspect of the subject matter disclosed in detail hereinafter is an automated apparatus for moving an end effector over a surface of an airfoil-shaped body having leading and trailing edges, comprising: a chassis comprising leading and trailing edge subassemblies which are movable relative to each other to change a state of the chassis from a first state to a second state; a plurality of rolling elements rotatably mounted to the leading and trailing edge subassemblies, the plurality of rolling elements being situated so that the airfoil-shaped body cannot be engaged with a gripping force when the chassis is in the first state and being situated so that the airfoil-shaped body can be engaged with a gripping force when the chassis is in the second state; a first actuator coupled to rotate one of the plurality of rolling elements when activated; a support assembly coupled to and displaceable along the chassis; a second actuator coupled to displace the support assembly when activated; an end effector coupled to and carried by support assembly; and a third actuator coupled to actuate operation of the end effector when activated. Optionally, the apparatus further comprises a fourth actuator coupled to change the state of the chassis from the first state to the second state when activated. In accordance with a further option, a fifth actuator could be arranged to raise and lower an end effector that is displaceable along a vertical arm. In accordance with one embodiment, a control computer located at an operations center is programmed to activate the actuators via an electrical cable. The end effector may comprise one of the following: a nondestructive inspection sensor, a drill motor or other rotary tool (such as a scarfer or grinder), a ply mapper, a squirter, a sprayer, a wiper, a continuous cleaning device, a roller that carries liquid and a suction or vacuum device for liquid runoff capture.

Another aspect is an automated apparatus for moving an end effector over a surface of an airfoil-shaped body having leading and trailing edges, comprising: a first support assembly comprising a forward body part, a rearward body part, and an intercostal element that interconnects the forward and rearward body parts, at least one of the forward and rearward body parts being displaceable along an axis of the intercostal element to facilitate adjustment of the distance separating the forward and rearward body parts; a first drive motor carried by the forward body part; a drive mechanism coupled to and depending from an output shaft of the drive motor and arranged to contact the airfoil-shaped body; a rolling element supported by the rearward body part and arranged to contact the airfoil-shaped body; a biasing mechanism coupled to the intercostal element and one of the forward and rearward body parts for exerting a force that urges the drive mechanism and the rolling element to grip the airfoil-shaped body; a guide element supported by the first support assembly; a second support assembly which is mounted on and displaceable along the guide element; and an end effector coupled to and carried by the second support assembly, wherein the first support assembly is displaceable in a spanwise direction along the airfoil-shaped body when the drive mechanism is driven by the drive motor, and the end effector is displaceable in a chordwise direction independent of spanwise displacement of the first support assembly.

A further aspect is an apparatus comprising a ladder, a frame member attached to the ladder, a height adjustment mechanism comprising a lower part attached to the ladder and an upper part which is coupled to the lower part of the height adjustment mechanism, a pair of cable pay-out rollers rotatably coupled to the frame member, and a grip attached to the upper part of the height adjustment mechanism, wherein the grip is configured to engage and stabilize a tip of a rotorcraft blade, and the height of the upper part of the height adjustment mechanism is adjustable by movement relative to the lower part.

Yet another aspect is a system comprising: an airfoil-shaped body having leading and trailing edges which extend from a root to a tip; a tip support assembly comprising a frame, a height adjustment mechanism comprising a lower part attached to the frame and an upper part which is coupled to the lower part of the height adjustment mechanism, first and second cable pay-out rollers rotatably coupled to the frame, and a grip attached to the upper part of the height adjustment mechanism and coupled to the tip of the airfoil-shaped body, wherein the height of the upper part of the height adjustment mechanism is adjustable by movement relative to the lower part; an automated blade crawler mounted to the airfoil-shaped body, the automated blade crawler comprising an end effector, first means for moving the blade crawler in a spanwise direction along the airfoil-shaped body, and second means for moving the end effector in a chordwise direction; and a cable having one end connected to the automated blade crawler and having another portion disposed between the first and second cable pay-out rollers.

Other aspects of the invention are disclosed and claimed below.

BRIEF DESCRIPTION OF THE DRAWINGS

FIG. 21A is a diagram showing a side view of a rotorcraft blade having an automated blade crawler mounted thereon, the blade tip being supported by a stabilizer in accordance with one embodiment. A frame of a cable payout roll assembly is not shown in FIG. 21A, but is shown in FIG. 21B.

FIG. 21B is a diagram showing a view of the rotorcraft blade stabilizer depicted in FIG. 21A.

Reference will hereinafter be made to the drawings in which similar elements in different drawings bear the same reference numerals.

DETAILED DESCRIPTION

U.S. patent application Ser. No. 12/657,424, in its broadest sense, disclosed an autonomous, self-propelled, expandable and adjustable apparatus for inspecting in-service airfoil-shaped structures such as rotorcraft blades, aircraft propellers, smaller winglets, and narrow tail sections for structural damage by crawling along the length of the airfoil-shaped structure using the structure itself as the track, and employing scanning sensor mechanisms such as ultrasonic pulse echo, eddy current arrays, resonance arrays, and bond tester or laser probes, to acquire data representing the structural conditions found as the inspection apparatus moves across the surface. Multiplexed pulser/receiver cards, and a controller within a computer with imaging software, can be cabled to the expandable crawler portion of the system to collect, display, and store NDI data.

Figure 1:
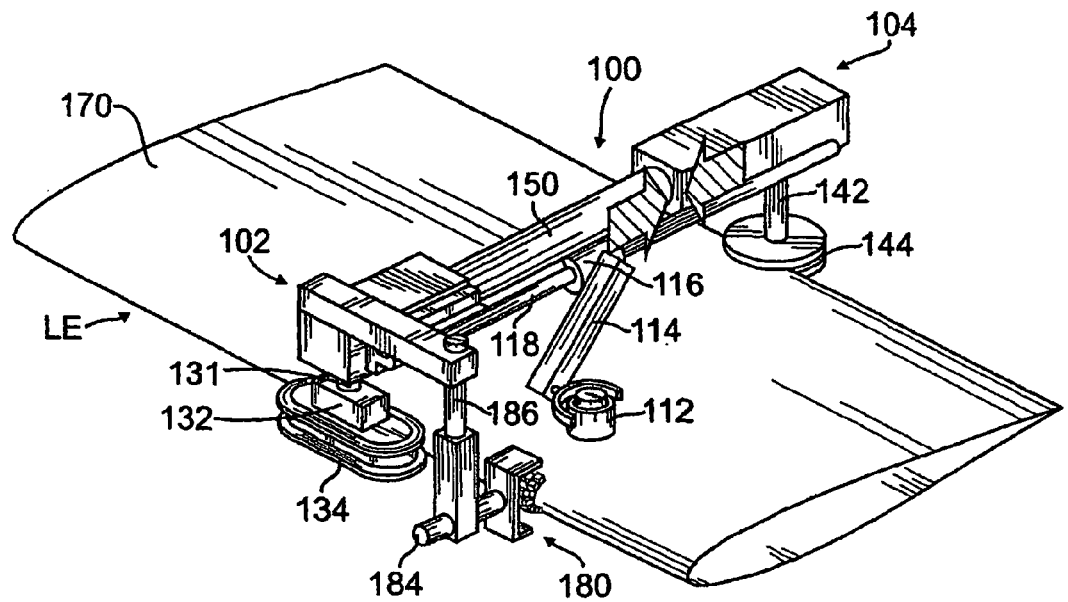
FIG. 1 is an isometric view of a blade crawler driven by a drive track 134, as disclosed in U.S. patent application Ser. No. 12/657,424, the crawler being mounted on an airfoil structure having a short chord length and carrying a nondestructive inspection sensor.

As seen in FIG. 1 (taken from U.S. patent application Ser. No. 12/657,424) an inspection apparatus 100 (hereinafter referred to as a "crawler") comprises a forward body part 102, a rearward body part 104, and an intercostal element 150 that interconnects the forward and rearward body parts to form a chassis. One of the forward and rearward body parts is displaceable along an axis of the intercostal element to facilitate adjustment of the distance separating the forward and rearward body parts, while the other body part is fixed relative to the intercostal element. For example, the intercostal element may comprise a circular cylindrical tube or rod having one end fixed to the forward body part 102, while a portion extending from the other end has the rearward body part 104 slidably mounted thereon in the manner of a telescoping sleeve, allowing the distance between the forward and rearward body parts to be adjusted to adapt to airfoil-shaped bodies having different chord lengths.

The forward body part 102 is positioned near a forward (i.e., leading) edge of the airfoil-shaped body 170 that is to be inspected, and the rearward body part 104 is positioned near an opposing (i.e., trailing) edge of the structure to be inspected. Inspection of the airfoil-shaped body 170 is carried out, in part, by a face-sheet scanner 112 pivotally mounted on one end of an arm 114, the other end of the arm 114 in turn being pivotably mounted to a slider 116 coupled to and slidable on a guide rod 118. (Alternatively, a guide rail or other guide element could be used in place of a guide rod). The face-sheet scanner 112 may comprise any one of a variety of NDI sensors to perform inspection of the airfoil-shaped body 170.

In accordance with one embodiment, scanner 112 follows the curved surface of the airfoil-shaped body 170 when arm 114 exerts a normal force on the pivotably supported scanner 112. The normal force keeps the scanner in intimate contact with the airfoil surface, thus enabling the NDI functionality of the scanner. In cases where the scanner comprises an array of ultrasonic transducers, acoustic couplant may be supplied from the operations center to the interface of the scanner and airfoil, for example, via a hose. The normal force exerted by the arm 114 can be generated by any conventional means, including the coupling of a spring, solenoid, pneumatic actuator or radial motion transducer (not shown in the drawings) between arm 114 and slider 116.

The forward body part 102 has a first rod 131 depending W therefrom on which is mounted a control motor 132. A drive wheel (not shown) is operatively connected to and supported from the control motor 132, the latter causing a drive track 134 to circulate the drive wheel and a second wheel (also not shown) while drive track 134 stays in frictional contact with the leading edge (LE in FIG. 1) of the airfoil-shaped body 170. Rotation of rod 131 causes the crawler 100 to travel in a spanwise direction provided that the drive track 134 does not slip relative to the leading edge.

Still referring to the embodiment depicted in FIG. 1, a second rod 142 depends from the rearward body part and carries a follower encoder wheel 144 on the free end thereof. The spanwise position of crawler 100 is measured by a rotary encoder (incorporated in the rearward body part 104), which encodes rotation of encoder wheel 144. The encoder wheel 144 rides on the airfoil surface as the crawler travels in the spanwise direction. The rotary encoder sends an encoder pulse to the operations control center (e.g., via an encoder cable or a wireless connection) after each incremental movement of crawler 100 in the spanwise direction, which encoder pulses are used by a control computer (not shown in FIG. 1, but see item 50 in FIG. 9, to be described in detail later) and by ultrasonic pulser/receiver devices (not shown in the drawings) to determine the spanwise coordinate of each scan plane in a well-known manner.

The drive track 134 and the encoder wheel 144 are held against, and in frictional engagement with, the leading and trailing edges, respectively, of the airfoil-shaped body 170 to be inspected. This is accomplished by application of a tensile force imparted to the forward and rearward body parts 102, 104 (to be discussed below). The front and rearward body parts in turn (in response to the tensile force applied between the front and rearward body parts) apply a compressive force on the blade component (via the drive track 134 and encoder wheel 144) that holds the crawler on the blade component. Preferably, drive track 134 is made of a material that frictionally engages the leading edge of the structural part being inspected so as to impart a driving force that moves the crawler 100 spanwise along the airfoil-shaped body 170. Additionally, the encoder wheel 144 tracks the spanwise position of the crawler 100 as it translates along the airfoil-shaped body 170.

The rearward body part 104 carries encoder wheel 144, which depends from, and is attached to, the rearward body part on a telescoping rod 142 that allows the vertical position of the encoder wheel to be adjusted to fit the trailing edge of the airfoil-shaped body 170. The drive track 134 and encoder wheel 144, in conjunction, exert a gripping force on the airfoil-shaped body 170 that holds the crawler 100 thereon. The gripping force can be generated by a spring (not shown) which extends between the intercostal element 150 and the rearward body part 104. In accordance with one embodiment, the spring has opposing ends attached to (for applying a tensile force between) the rearward body part 104 and one of a plurality of attachment points spaced along the length of the intercostal element 150.

Figure 6:
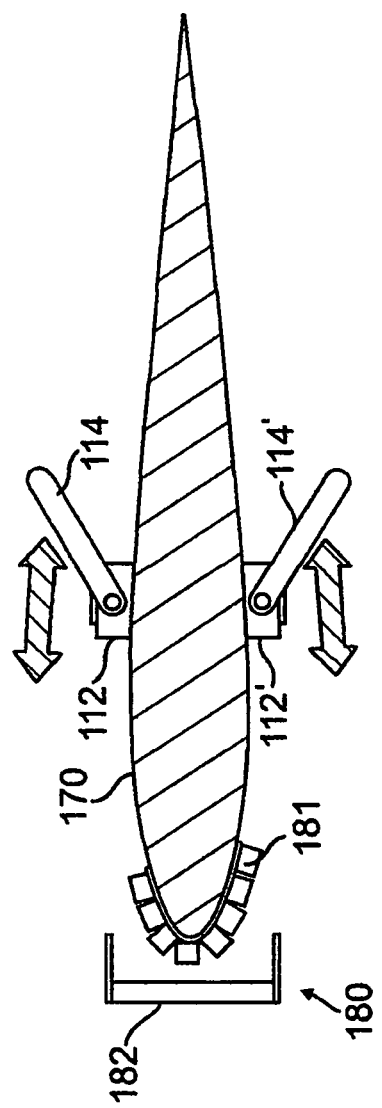
FIG. 6 is a diagram showing some components of a blade crawler in accordance with a further embodiment (disclosed in U.S. patent application Ser. No. 12/657,424) that is capable of performing nondestructive inspection on the top and bottom surfaces and along the leading edge of the airfoil concurrently. Again, for the purpose of simplicity, a solid airfoil has been shown in section, although most airfoils have a hollow internal structure.
Figure 7:
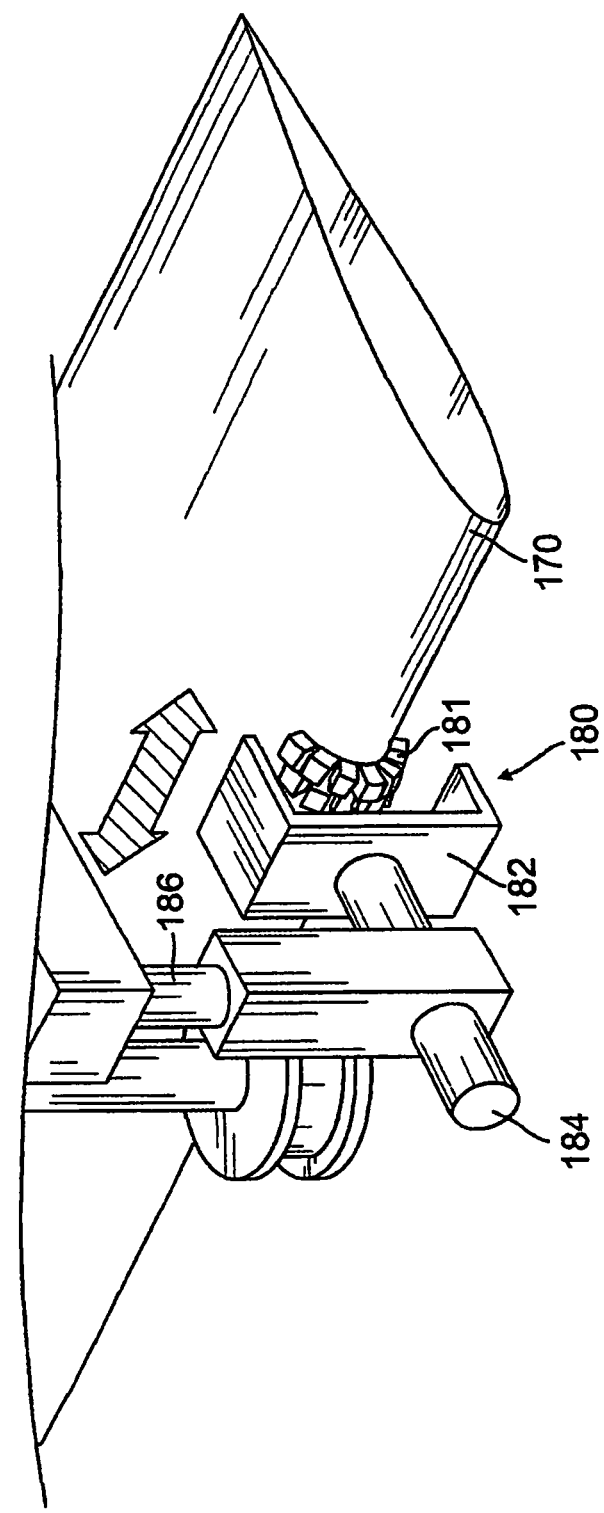
FIG. 7 is an isometric view of the leading edge scanning assembly 180 shown in FIG. 3. This same leading edge scanning assembly can be incorporated in the embodiment shown in FIG. 6.

The forward body part 102 also carries a leading edge scanner assembly 180 that supports a leading edge sensor array 181 (see FIGS. 6 and 7 and the accompanying discussion for a detailed description of leading edge scanner assembly 180). Inside the leading edge scanner assembly 180 (see FIG. 7), sensor array 181 is conformably supported by a leading edge scanner frame 182 which is horizontally adjustable toward and away from the leading edge of the airfoil-shaped body 170 on adjustment rod 184, and vertically adjustable relative to the leading edge of the airfoil-shaped body 170 on a second adjustment rod 186.

Various types of sensors may be utilized to perform non-destructive testing. One or more sensors may move over the portion of the structure to be examined, and receive data regarding the structure. For example, a pulse-echo, thru-transmission, or shear wave sensor may be utilized to obtain ultrasonic data, such as thickness gauging, detection of laminar defects and porosity, and/or detection of cracks in the structure. Resonance, pitch/catch or mechanical impedance sensors may be utilized to provide indications of voids or porosity, such as in adhesive bondlines of the structure. In addition, single and dual current eddy current sensors impart and detect eddy currents within a structure so as to identify cracks and/or corrosion, particularly in metallic or other conductive structures. The data acquired by the sensors is typically processed by a processing element, and the processed data may be presented to a user via a display in a conventional manner.

Referring again to FIG. 1, to translate the face sheet scanner 112 chordwise across the airfoil-shaped body 170, it is contemplated that a motor will be encased within the slider 116 to interact with the guide rod 118 via gears or friction wheels. Alternatively, the chordwise motion may be achieved by positioning the motor on the forward body part 102 and translating the slider 116 via a cable, drive belt, chain, or screw-drive in a well-known manner.

Figure 2:
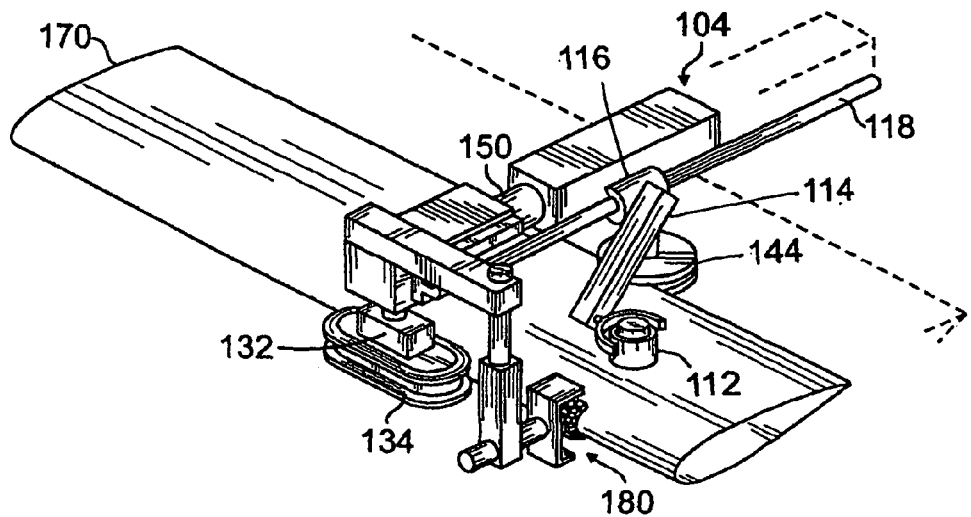
FIG. 2 is an isometric view of the apparatus depicted in FIG. 1, mounted on an airfoil structure having a relatively shorter chord length.

FIG. 2 shows the crawler 100 of FIG. 1 mounted on a airfoil-shaped body 170 having a chord length less than the chord length of the airfoil-shaped body 170 shown in FIG. 1. As described previously, a tensile force can be applied by an internal tension spring that extends between an attachment point (not shown) on the intercostal element 150 and an attachment point (not shown) on the movable rearward body part 104. Multiple attachment points can be provided on the intercostal element 150 so that a spring tension within desired operational limits can be maintained during respective inspections of blades having different chord lengths. When one end of the tension spring is unlooked from a current attachment point, the rearward body part 104 can be translated along the intercostal element 150 in either direction and then the tension spring can be hooked onto a new attachment point, selected to produce a desired spring tension. In this manner, the crawler 100 can be expanded or retracted to accommodate structural elements having a range of chord lengths, as illustrated in FIGS. 1 and 2.

Figure 3:
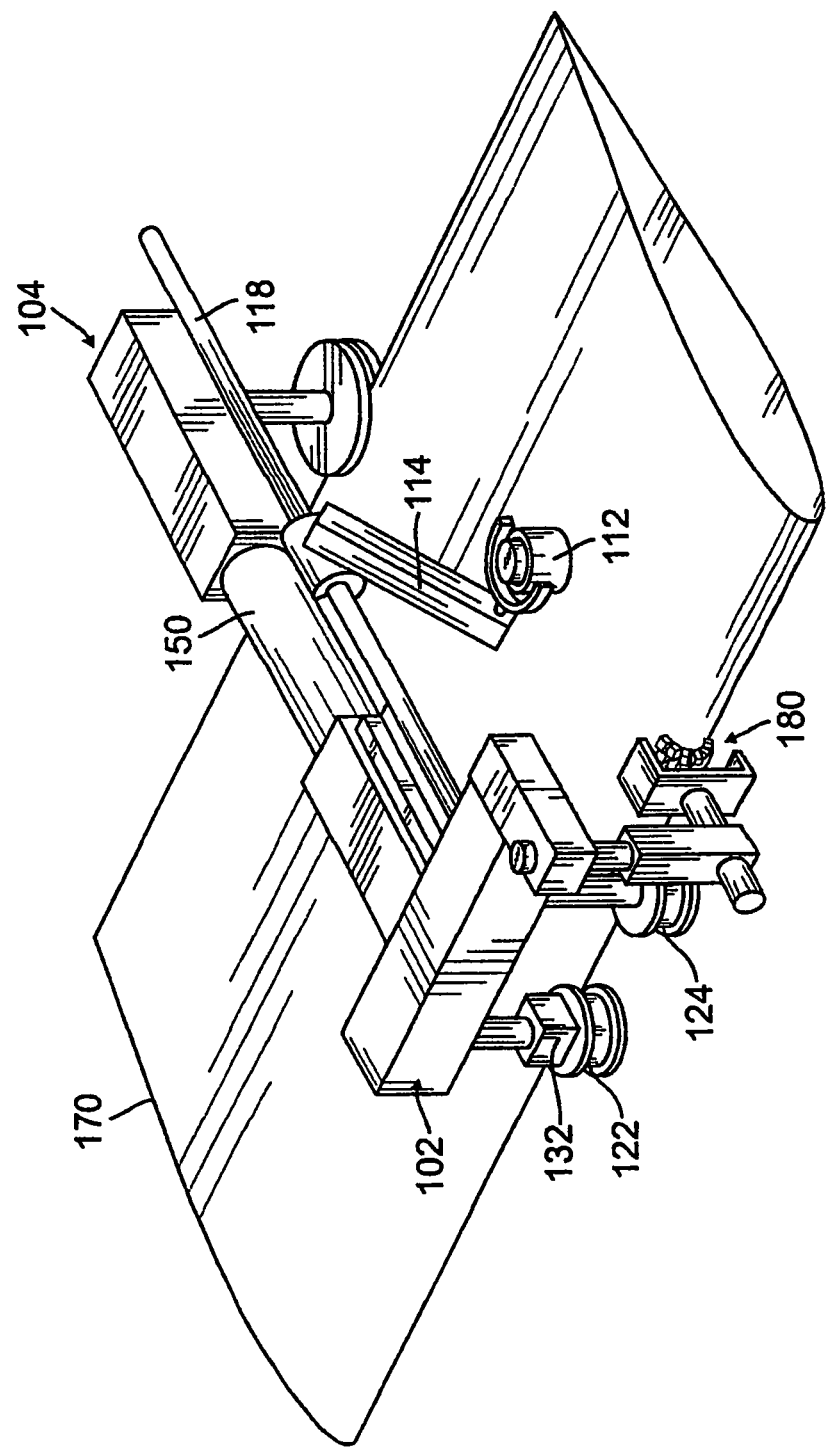
FIG. 3 is an isometric view of a variation of the apparatus depicted in FIG. 1 in which the drive track 134 has been replaced by a drive roller 122 and a follower wheel 124.

FIG. 3 shows a second embodiment of crawler 100 that includes the same elements depicted in FIG. 1, except that the drive track shown in FIG. 1 has been replaced by a drive roller 122 operatively coupled to the control motor 132 (carried by forward body part 102) and a secondary follower wheel 124 displaced spanwise from the drive wheel (also carried by forward body part 102).

Figure 4:
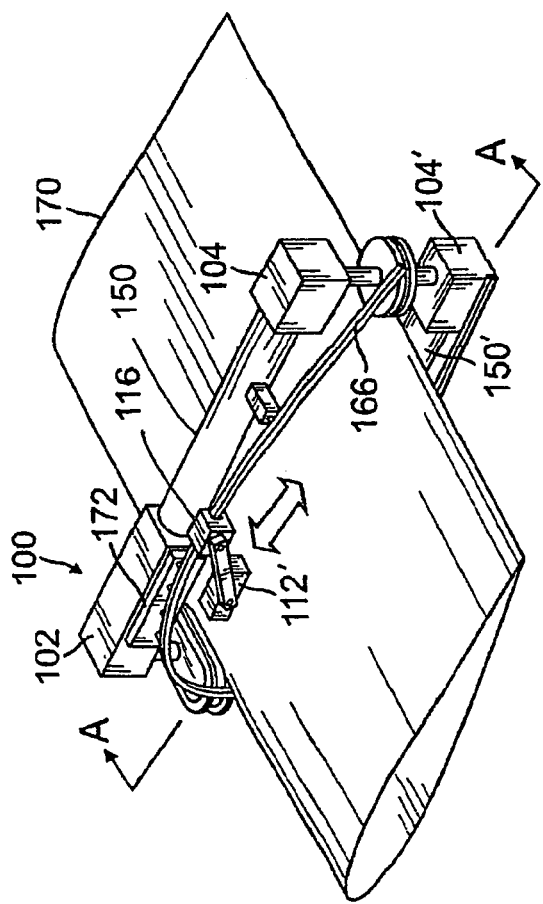
FIG. 4 is an isometric view of a blade crawler in accordance with an alternative embodiment (also disclosed in U.S. patent application Ser. No. 12/657,424) that is capable of performing nondestructive inspection on the top surface, the leading edge and the bottom surface of the airfoil structure in sequence.
Figure 5:
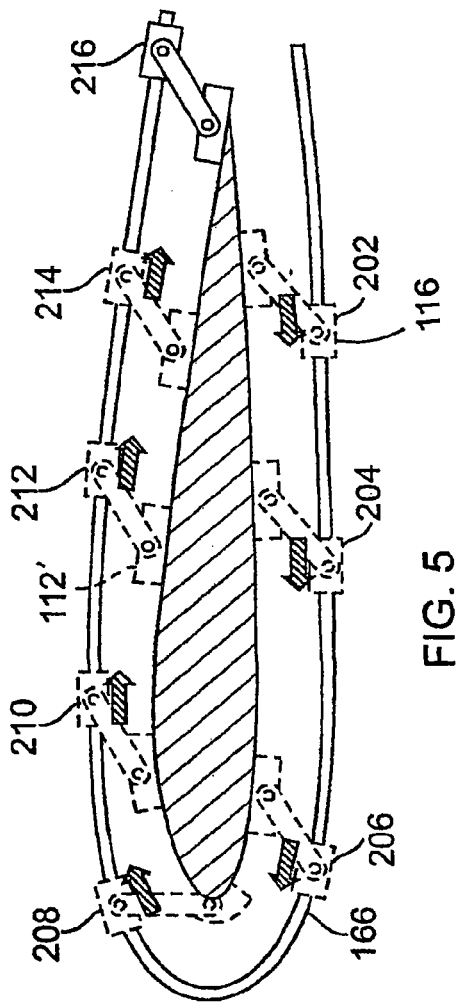
FIG. 5 is a diagram showing some components of the blade crawler depicted in FIG. 4 and showing the airfoil in section, the section being taken along a section line A-A indicated in FIG. 4. For the purpose of simplicity, this sectional view through the airfoil indicates that the airfoil in the sectional plane is solid material. However, it should be understood that most airfoils have a hollow internal structure, e.g., a honeycomb-like structure.

FIGS. 4 and 5 depict a further embodiment in which the structural element can be scanned around its entire periphery using a crawler 100 having a continuous guide rod 166 supported by upper and lower chasses having structures which mirror each other. The upper chassis comprises forward body part 102, intercostal element 150 [Not on figure] and rearward body part 104 positioned above the airfoil-shaped body 170, while the lower chassis comprises a second forward body part (hidden in FIG. 4), intercostal element 150' and rearward body part 104' positioned below the airfoil-shaped body 170. The upper and lower chassis, in conjunction with the drive track and encoder wheel (and their axles), form a crawler capable of travel in a spanwise direction when mounted on the airfoil-shaped body 170.

The continuous guide rod 166 can be integrally formed with a pair of mounting plates 172 (only the upper mounting plate is visible in FIG. 4) that are fastened to the respective forward body parts of the upper and lower chasses. As best seen in FIG. 5, the continuous guide rod 166 supports the slider 116 to which a NDI scanner element 112' is attached. The continuous guide rod 166 extends, with a gradual curvature, from the rearward body part to the forward body part of the upper chassis (not shown in FIG. 5), and then, with a reduced radius, extends from the forward body part of the upper chassis to the forward body part of the lower chassis (not shown in FIG. 5), and then extends toward the rearward body part of the lower chassis. The slider 116 may comprise an encased motor that interacts with the continuous guide rod 166 along its entire length via gears or friction wheels.

FIG. 5 depicts the path of travel of the face-sheet scanner 112' as it moves around the airfoil-shaped body from an initial position 202 at the bottom of the airfoil trailing edge to a final position 216 at the top of the airfoil trailing edge. The face-sheet scanner 112' can be indexed in a conventional manner, taking measurements (e.g., ultrasonic scanning in a scan plane) at the initial position and each incremental position thereafter until the final position is reached. The initial position 202 and a multiplicity of intermediate positions 204, 206, 208, 210, 212, and 214 are shown in phantom in FIG. 5.

The position of slider 116 relative to the continuous guide rod 166 can be measured by a second encoder incorporated in the motor that drives slider travel along the guide rod. The relationship of slider position (relative to the guide rod) to scanner position (relative to the airfoil) can be determined empirically and used by the control computer to determine the scanner position as a function of the pulses from the second encoder, which encoder pulses are used by a control computer and by the ultrasonic pulser/receiver devices to determine the chordwise coordinates of the acquired scan data. Alternatively, an encoder wheel could be mounted to the scanner in a manner such that it rolls along the airfoil surface as the scanner is moved in a chordwise direction.

FIG. 6 shows some components of a blade crawler in accordance with a further embodiment that is capable of performing nondestructive inspection concurrently on the top and bottom surfaces and along the leading edge of the airfoil-shaped body. A pair of NDI scanner elements 112, 112' are respectively mounted to the distal ends of respective arms 114, 114', the proximal ends of which are coupled to respective sliders (not shown in FIG. 6) which travel along respective upper and lower guide rods (not shown in FIG. 6) to enable simultaneous inspection of the upper and lower surfaces of the airfoil-shaped body 170. This embodiment is similar to the embodiment shown in FIG. 4 in that it has upper and lower chasses which mirror each other, but instead of a common guide rod that passes around the airfoil leading edge, there are two separate guide rods.

FIG. 7 shows the leading edge scanning assembly 180 depicted in FIG. 3, but on a magnified scale. This same leading edge scanning assembly can be incorporated in the embodiment shown in FIG. 6. Referring to FIG. 7, the leading edge scanning assembly 180 comprises a leading edge scanner array 181 carried by leading edge scanner frame 182 and positioned at the leading edge of the airfoil-shaped body 170. The leading edge scanner frame 182 can take the form of an expandable bladder, a foam member, or an elastomeric member that causes the sensors to conform to the leading edge of the airfoil-shaped body 170. Alternatively, the leading edge scanner frame 182 can include a plurality of spring elements disposed between the inner surface of leading edge scanner frame 182 and adjacent surfaces of the leading edge scanner array 181. Other arrangements may also be used, such as a series of pivots or hinges, to orient the elements of the leading edge sensor array 181 to be normal to confronting surface areas of the leading edge. As shown by the double-headed arrow in FIG. 7, the crawler and the leading edge scanning assembly 180 supported thereon can be moved in a spanwise direction so that the entire leading edge of the airfoil-shaped body 170 can be scanned.

Figure 9:
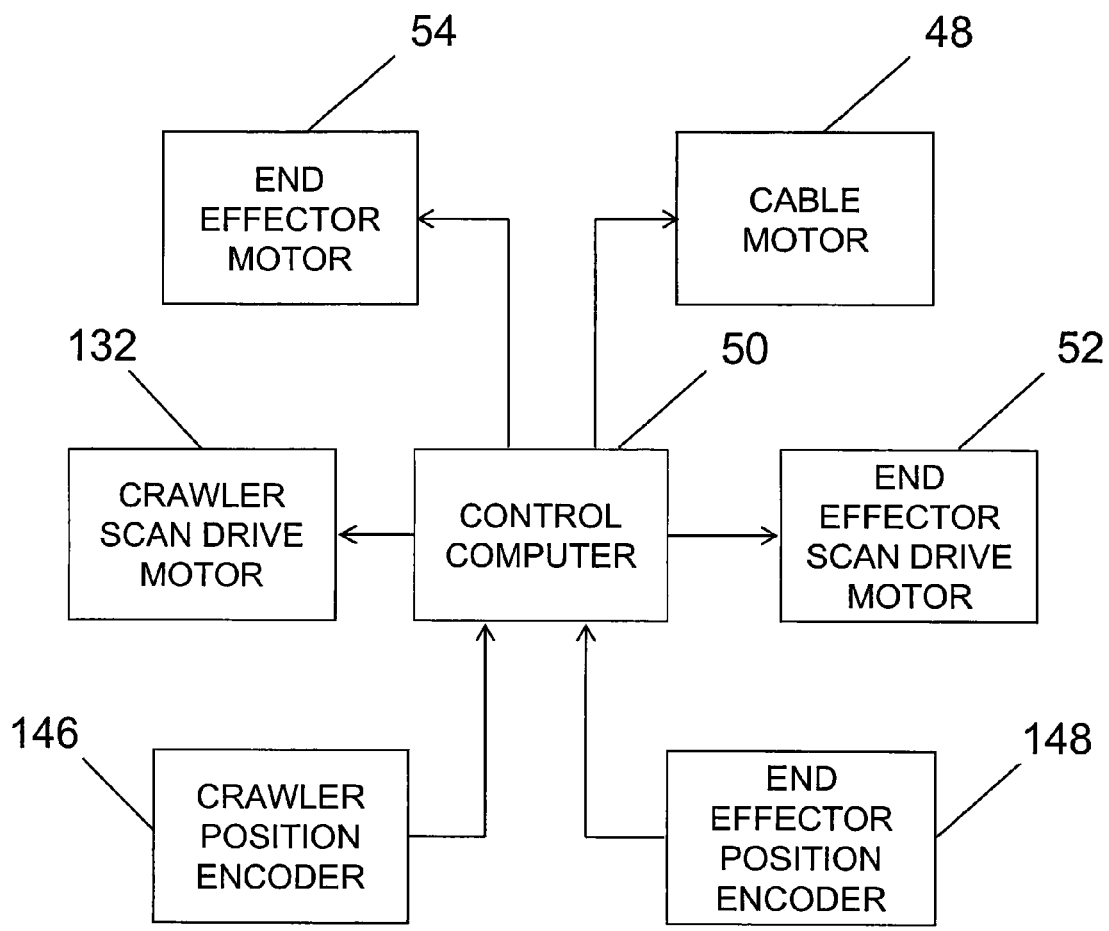
FIG. 9 is a block diagram showing communications between a control computer and various components of a blade crawler in accordance with one embodiment.

Data developed by the sensing elements 112 or 112', as well as by the leading edge sensor array and the positional encoding mechanisms, are fed as analog or digital signals to a central computer (item 50 in FIG. 9). The resulting output of the central computer can then be fed to a display device, such as a computer-driven display, thereby permitting an operator to view results being obtained. This visual information gives an operator the opportunity to make appropriate adjustments to the scanner apparatus to ensure the desired scanning information is obtained.

The blade crawler described above can also be adapted for use in the automation of various maintenance functions, including but not limited to nondestructive inspection, drilling, grinding, fastening, appliqué application, scarfing, ply mapping, depainting, cleaning and painting. There are a number of types of blade components on aircraft that will benefit from maintenance automation, including helicopter blades, propeller blades, flaps, ailerons, trim tabs, slats, stabilators and stabilizers. These operations enable the blade crawler to reduce maintenance time, reduce maintenance labor and reduce human error—all through automation of these normally manual processes.

Figure 8:
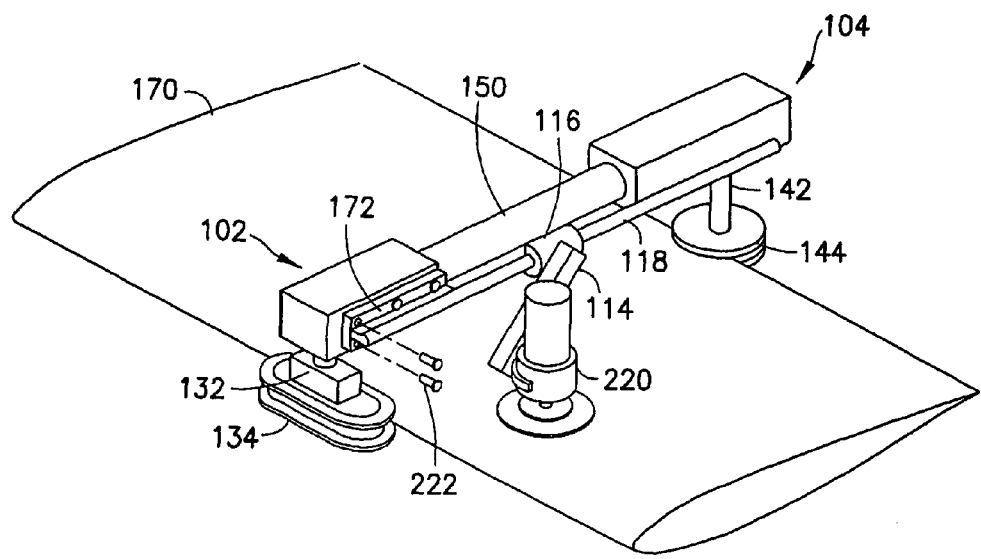
FIG. 8 is a diagram showing an isometric view of a rotary scarfer supported on an adjustable chassis of a blade crawler, the adjustable chassis comprising a telescoping sleeve.

FIG. 8 shows a rotary scarfer 220 supported by an adjustable chassis (comprising components 102, 104 and 150 as previously described) of a blade crawler. The rotary scarfer 220 is pivotably mounted to the distal end of arm 114, the proximal end of which is pivotably mounted to slider 116 as previously described. Alternatively, the rotary scarfer 220 can be mechanically oriented to achieve specific angularities using a variety of powered mechanisms for changing an orientation, such as solenoids, pneumatic actuators or radial motion transducers. The slider 116 slides along a guide rod 118 which is integrally formed with a mounting plate 172 that is fastened to the forward body part 102 by a plurality of fasteners 222.

While FIG. 8 shows an embodiment in which the end effector is a rotary scarfer, it should be appreciated that other types of end effectors can attached to the distal end of arm 114. The rotary scarfer 220 may be pneumatically driven via a hose (not shown in FIG. 8) supplying pressurized air from the operations center. The spanwise position of the blade crawler 100, the chordwise position of the rotary scarfer, and the operation of the rotary scarfer (or other end effector) can be controlled by the operations central computer in accordance with a pre-programmed maintenance operation. It is also possible for the system operator to manually control functions by means of a joystick or numeric commands typed on a keyboard.

For many blade components made of laminated composite material, scarfing to eradicate skin damage is a common maintenance function. The automated scarfing involves the removal of material (i.e., auguring) by means of milling using a high-speed rotary bit or mechanical sanding using an abrasive pad. Auguring is often performed in order to prepare a component surface for a hot bond repair. For example, plies of composite material could be removed in a damaged area to form a cavity suitable for receiving a stack of plies of composite material designed to form a repair patch when cured in place. The use of an automated blade crawler carrying a rotary scarfer would relieve mechanics of the tedious job of locating scarf areas and precisely sanding or milling to remove damaged plies of composite material. Alternatively, a grinding tool could be substituted for the rotary scarfer for removing bonded or bolted components.

For many blade components, ply mapping as a prelude to the application of a repair patch is a common maintenance function. A ply mapper could be substituted for the rotary scarfer 220 seen in FIG. 8 and could comprise a digital photographic device or a touch probe device to define the shape of the cavity formed during the scarfing operation. The goal is to acquire a three-dimensional measurement of the cavity, including measurements indicating the shape of the cavity and lateral dimensions of the cavity at various depths. Based on this information, plies having the appropriate shape and lateral dimensions can be cut and stacked in the cavity for creating a repair patch. Often accomplished to automatically define the contour of each repair ply, an automated ply mapper blade crawler would relieve mechanics of the tedious job of manually mapping the plies for a repair patch.

For many blade components, drilling is a common maintenance function. Optionally the blade crawler disclosed herein may be equipped with an automated driller to create holes for fasteners. Such a blade crawler would relieve mechanics of the tedious job of locating holes, drilling to exact specifications, countersinking and deburring.

For many blade components, depainting is a common maintenance function. Optionally the blade crawler disclosed herein may be equipped with an automated depainter. Automated depainting using the blade crawler disclosed herein could include mechanical sanding, automated chemical application, rinse and collection, or automated media blast with debris collection. Often accomplished to remove old paint from the component surface, an automated depainter blade crawler would relieve mechanics of the tedious job of precision hand sanding, media blasting, vacuuming away liquid, dust and debris, or chemical treatment.

For many blade components, cleaning is a common maintenance function. Optionally the blade crawler disclosed herein may be equipped with an automated cleaner. An automated blade crawler for cleaning would include a set of end effectors, including a cleaning solution squirter, an automated wiper/scrubber/buffer, and a rinse solution squirter along with a vacuum collection device. Often accomplished to remove dirt and debris from the component surface, an automated cleaning blade crawler would relieve mechanics of the tedious job cleaning large areas on the blade component.

For many blade components, painting is a common maintenance function. Optionally the blade crawler disclosed herein may be equipped with an automated painter. The automated painting end effector devices could include sprayers, rollers and applicators along with a vacuum collection system. Often accomplished to recover the component surface, an automated painter blade crawler would relieve mechanics of the tedious job of precision hand painting of the blade component.

FIG. 9 is a block diagram showing communications between a control computer 50 and various components of an end effector-carrying blade crawler in accordance with one embodiment. In this instance, the control computer 50 is connected to the blade crawler by an electrical cable (not shown). (Alternatively, the control computer and the blade crawler could communicate wirelessly). The control computer 50 may be programmed to control a cable management system (not shown). For example, motion control application software running on computer 50 can control a cable motor 48 of the cable management system. When the blade crawler is operated, one or more cables need to accompany the crawler down the length of the airfoil-shaped body, e.g., a helicopter blade. The motion control software running on computer 50 synchronizes the movement of the cables with the movement of the blade crawler, extending or retracting the cables as appropriate. The computer system is programmed to control the cable motor 48 in dependence on crawler spanwise-position information derived from pulses generated by a crawler position encoder 146 (e.g., coupled to encoder wheel 144 seen in FIG. 1). In addition, the control computer 50 controls the crawler scan drive motor 132 in dependence on the pulses from crawler position encoder 146.

When the crawler reaches a target spanwise position, the control computer 50 shuts off the crawler scan drive motor 132 and then starts an end effector scan drive motor 52, e.g., a drive motor which moves slider 116 along the guide rod 118 seen in FIG. 1. The computer system is programmed to control the end effector scan drive motor 52 in dependence on the end effector chordwise-position information derived from pulses generated by an end effector position encoder 148.

In cases where the end effector is a rotary tool (such as a scarfer, drill, deburrer or reamer), when the rotary tool reaches a target chordwise position, the control computer 50 shuts off the end effector scan drive motor 52 and then starts an end effector motor 54, e.g., a drive motor which drives rotation of the rotary tool. It should be appreciated that in cases where the end effector is emitting or ingesting a liquid or particles, the control computer will activate a pump. In cases where the end effector's elevational position is adjustable by operation of an actuator, such actuator may also be controlled by the computer.

Alternatively, in cases where a motion-producing device (such as a motor, solenoid, piston, etc.) is actuated to cause the crawler to grip the airfoil-shaped body, actuation of that motion-producing device may also be controlled by the control computer 50.

An automated blade crawler carrying any one of a multiplicity of end effectors, as disclosed above, may also have any one of a multiplicity of configurations that enable movement, positional tracking and traction along an airfoil component. Included in these configurations are multiple options for wheels and/or rollers, grip mechanism, positional tracking mechanisms, and braking devices. These configurations operate in conjunction to enable the functions that ensure that the crawler deploys effectively. As a whole, the blade crawler reduces maintenance time, lab or hours and human errors when NDI or maintenance are performed on blade components.

As part of the crawling automated scanner apparatus, the movement and alignment mechanisms perform multiple functions that enable the entire apparatus to operate in the NDI or maintenance modes: (1) causing the apparatus to move in a spanwise direction along the blade; (2) tracking the spanwise position of the apparatus relative to the blade; and (3) ensuring that the apparatus does not slip along the blade. More specifically, the chassis of the crawler should be capable of locomotion along the blade component; the spanwise position of the chassis along the blade component should be tracked to enable the operations of the apparatus to be properly conducted; and during operations where side and normal forces are acting on the end effector, the apparatus should maintain a constant position along the spanwise direction of the blade component These functions are enabled by components of the movement and alignment mechanisms which are detailed in the following sections respectively entitled: (A) Wheel Configurations; (B) Chordwise Grip Mechanism Configurations; (C) Positional Tracking Mechanisms; and (D) Brake Configurations.

Wheel Configurations

In the embodiment shown in FIG. 8, the blade crawler grips the airfoil-shaped body by means of a drive track 134 in contact with the leading edge and an encoder wheel 144 in contact with the trailing edge. Many other roller/wheel configurations can be used in place of a drive track at the leading edge to move the crawler. For example, either a grooved or a flat drive roller, with or without alignment rollers or wheels, can be used to apply the driving force at or near the leading edge for causing spanwise displacement of the crawler. The wheels convert kinetic energy from a rotating shaft into work that moves the crawler along airfoil-shaped body.

Figure 10:
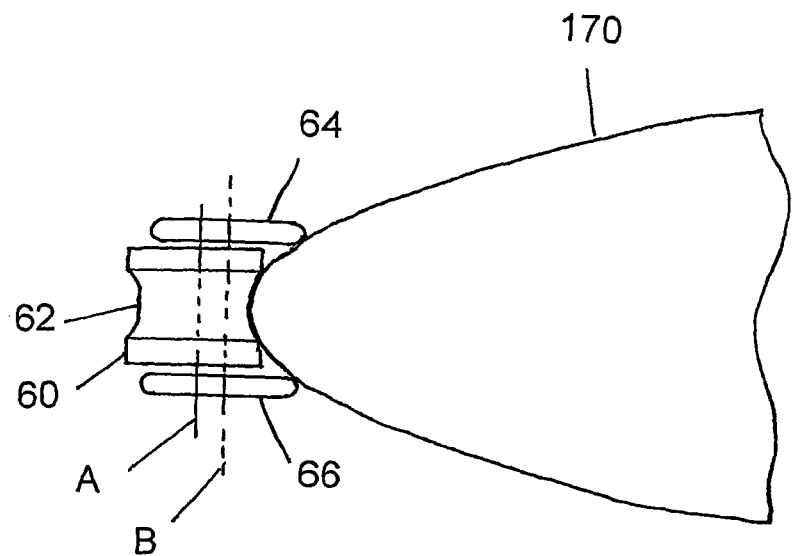
FIG. 10 is a diagram showing a grooved drive roller and a pair of parallel-axis alignment wheels in contact with a leading edge of an airfoil-shaped body in accordance with one embodiment.

FIG. 10 shows a grooved drive roller 60 and a pair of parallel-axis alignment wheels 64 and 66 in contact with a leading edge of an airfoil-shaped body 170 in accordance with one embodiment. The drive roller 60 may have a curved groove 62 that matches or nearly matches the curved profile of the leading edge, or the groove may be V-shaped. The drive roller 60 is preferably made of a high-traction material that ensures a positive grip when the drive roller applies contact pressure on the leading edge of the airfoil-shaped body 170. Alignment wheels 64, 66 may be arranged to have a common axis of rotation B that is parallel to, but displaced from the axis of rotation A of the drive roller 60, i.e., multiple parallel axles with independent housings. Alignment is ensured when the grooved drive roller 60 and alignment wheels 64, 66 trap the contour of the leading edge. Alternatively, the drive roller 60 and alignment wheels 64, 66 could have a common axis of rotation or the alignment wheels 64, 66 could have non-parallel axes of rotation (see alignment wheel axes of rotation C and D in FIG. 11).

Figure 11:
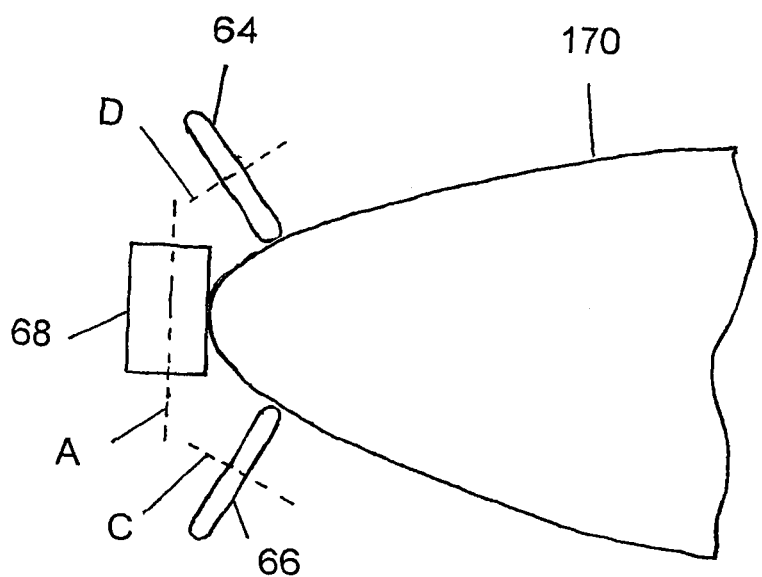
FIG. 11 is a diagram showing a flat drive roller and a pair of off-axis alignment wheels in contact with a leading edge of an airfoil-shaped body in accordance with another embodiment.

FIG. 11 shows a flat (i.e., circular cylindrical shape) drive roller 68 and a pair of off-axis alignment wheels 64 and 66 in contact with a leading edge of an airfoil-shaped body 170 in accordance with another embodiment. The drive roller 68 is preferably made of a high-traction material that ensures a positive grip when the drive roller applies contact pressure. Alignment is ensured when the flat drive roller 68 and alignment wheels 64, 66 trap the contour of the leading edge. Alternatively, alignment wheels 64, 66 may be arranged to have a common axis of rotation that is parallel to, but displaced from the axis of rotation A of the flat drive roller 68 (similar to the arrangement seen in FIG. 10), or the flat drive roller 68 and alignment wheels 64, 66 could have a common axis of rotation.

Figure 12:
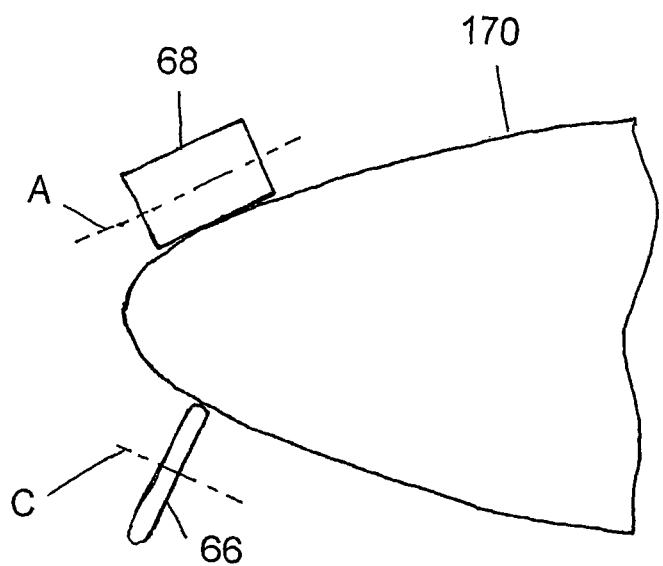
FIG. 12 is a diagram showing a flat drive roller and a single off-axis alignment wheel in contact with a leading edge of an airfoil-shaped body in accordance with a further embodiment.

FIG. 12 shows a further alternative configuration in which a flat drive roller 68 is arranged to contact an upper surface area that is part of or located near the leading edge of the airfoil-shaped body 170 and a single off-axis alignment wheel 66 is arranged to contact a lower surface area that is part of or located near the leading edge of the airfoil-shaped body 170. Alignment is ensured when the flat drive roller 68 and alignment wheel 66 trap the contour of the leading edge. Alternatively, the positions of flat drive roller 68 and alignment wheel 66 could be switched.

Flat or grooved alignment rollers (no drive function) could be used in place of alignment wheels in any one of the configurations disclosed herein. Also tracked alignment wheels with no drive function could be employed.

Figure 13:
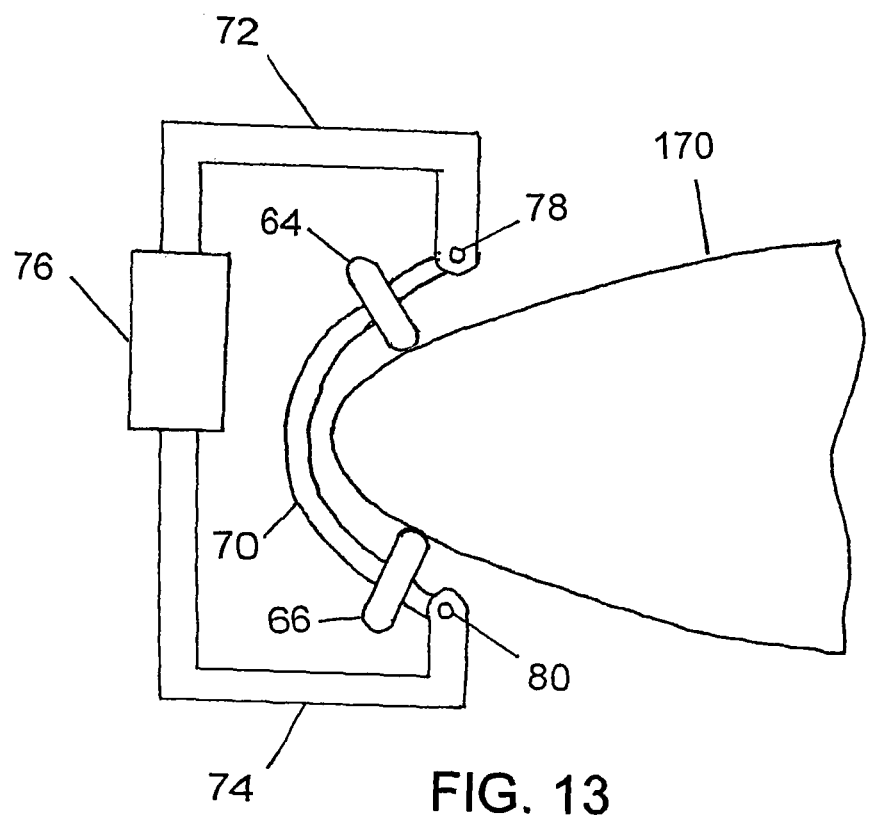
FIG. 13 is a diagram showing a pair of off-axis alignment wheels in contact with a leading edge of an airfoil-shaped body, the alignment wheels being rotatably mounted on a flexible axle in accordance with another embodiment.

FIG. 13 shows a pair of off-axis alignment wheels 64, 66 in contact with a leading edge of an airfoil-shaped body 170, the alignment wheels being rotatably mounted on a flexible axle 70 in accordance with a further embodiment. The flexible axle may be made of metal or metal alloy, polymeric material, spring material, or other suitable material. The flexible axle support assembly comprises a rigid upper arm 72 having one end pivotably coupled to one end of the flexible axle 70 by a pivot joint 78 and another end threadably coupled to one end of an expansion sleeve 76; and a rigid lower arm 74 having one end pivotably coupled to the other end of flexible axle 70 by a pivot joint 80 and another end threadably coupled to the other end of expansion sleeve 76. The threads coupling the expansion sleeve 76 to arms 72 and 74 are configured so that rotation of sleeve 76 in one direction causes the opposing threaded ends of arms 72 and 74 to move further apart (also causing pivot joints 78 and 80 to move further apart), whereas rotation of sleeve 76 in the opposite direction causes the opposing threaded ends of arms 72 and 74 to move closer to each other (also causing pivot joints 78 and 80 to move closer together). The radius of curvature of the flexible axle 70 decreases as pivot joints 78 and 80 move toward each other, and increases as pivot joints 78 and 80 move away from each other, thereby allowing the positions of alignment wheels 64 and 66 to be adjusted to better fit the contour of the leading edge of airfoil-shaped body 170. The flexible axle 70 also conforms under pressure to the shape of the leading edge. The alignment mechanism shown in FIG. 13 may be used in conjunction with a drive track or one or more drive rollers of a type previously described.

Optionally, position encoders may be provided which output pulses representing the rotation of encoder wheels which respectively engage the trailing and leading edges of the airfoil-shaped body. These encoder pulses are transmitted to the control computer, which is programmed to monitor the respective displacements of those encoder wheels along both edges and then compensate if the crawler begins to rotate during spanwise translation.

Chordwise Grip Mechanism Configurations

Any one of a multiplicity of chordwise grip mechanisms can be employed to enable the movement and alignment mechanism functions. Each chordwise grip mechanism causes the wheels to act on the blade leading and trailing edges by imparting a normal force to the wheels. One or more chordwise grip mechanisms may be employed on an apparatus to provide optimum functionality.

One suitable chordwise grip mechanism configuration is the linear telescoping sleeve mechanism previously described with reference to FIG. 1. A sufficient gripping force is generated when the telescoping sleeve (i.e., the rearward body part 104) retracts, causing the drive roller and alignment wheels to engage the leading edge and the encoder wheel (which also functions as an alignment wheel) to engage the trailing edge. Any one of a multiplicity of known linear motion devices can be employed to cause the rearward body part 104 to retract relative to the intercostal element 150, including the following: a solenoid, a piston, a rack and pinion assembly, a spring, or other translation mechanism.

Alternative chordwise grip mechanism configurations are shown in FIGS. 14-18.

Figure 14:
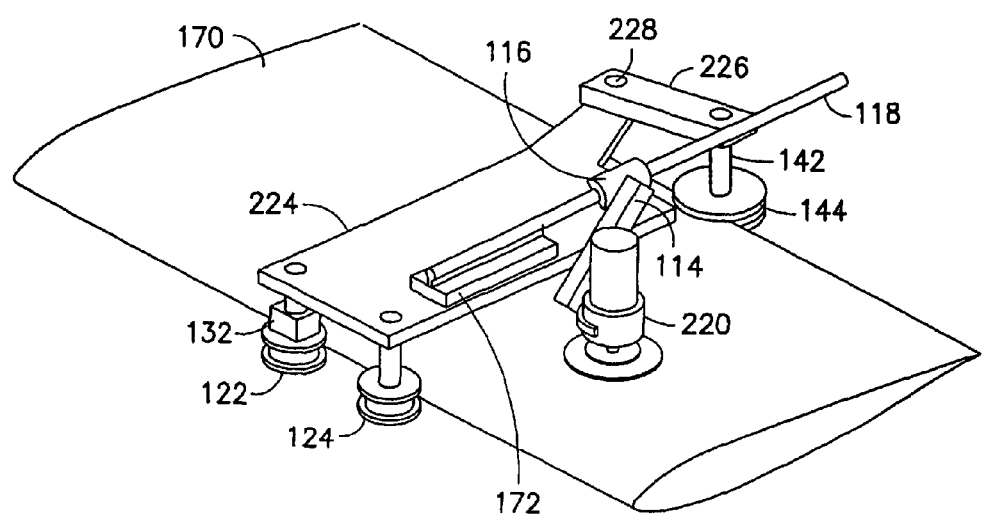
FIG. 14 is a diagram showing an isometric view of portions of a blade crawler in accordance with an alternative embodiment in which the crawler carries a rotary scarfer and the adjustable chassis comprises a chordwise grip mechanism having a pincers configuration.

FIG. 14 is a diagram showing an isometric view of portions of a blade crawler in accordance with an alternative embodiment in which the crawler carries a rotary scarfer 220 and the adjustable chassis comprises a chordwise grip mechanism having a pincer configuration. Instead of using a linear telescoping sleeve mechanism as shown in FIG. 3, the chordwise grip mechanism depicted in FIG. 14 comprises a frame 224 and a pincer arm 226, one end of which is pivotably coupled to frame 224 by a pivot joint 228 and the other end of which supports rod 142 that carries the encoder wheel 144. Mounting plate 172, which is integrally formed with the guide rod 118, is fastened to the frame 224. Frame 224 also supports the drive motor 132 and follower wheel 124. A sufficient gripping force is generated when the pincer arm 226 is rotated into a position in contact with the trailing edge of the airfoil-shaped body 170, sufficient force being applied to cause the drive roller 122 and follower wheel 124 to engage the leading edge while the encoder wheel 144 engages the trailing edge. Any one of a multiplicity of known radial motion devices (not shown in FIG. 14) can be employed to apply the torque on pincer arm 226, such as a motor, a screw drive lever, a rack and pinion assembly, or a torsion spring.

In accordance with an alternative chordwise grip mechanism, one end of a second pincer arm could be pivotably mounted on the other end of frame 224, while the other end of the second pincer arm supports the axle of follower wheel 124. In this embodiments having a pincers configuration, the first pincer arm (item 226 in FIG. 14) would be rotated into contact with the trailing edge, while the second pincer arm would be rotated into contact with the leading edge to create the desired chordwise gripping force.

Figure 15:
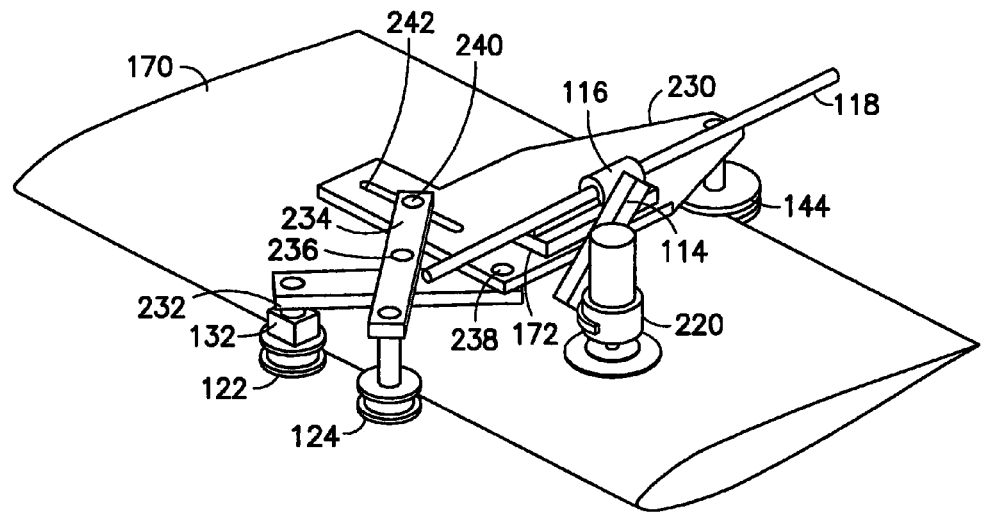
FIG. 15 is a diagram showing an isometric view of portions of a blade crawler in accordance with another embodiment in which the crawler carries a rotary scarier and the adjustable chassis comprises a chordwise grip mechanism having a scissors configuration.

FIG. 15 shows portions of a blade crawler in accordance with an alternative embodiment in which the crawler carries a rotary scarfer 220 and the adjustable chassis comprises a chordwise grip mechanism having a scissors configuration. This chordwise grip mechanism comprises a frame 230 and a pair of scissor arms 232 and 234 which are pivotably coupled at their midpoints by a pivot joint 236. One end of scissor arm 232 is pivotably coupled to frame 230 by a pivot joint 238 and the other end of scissor arm 232 supports drive motor 132. One end of scissor arm 234 carries a pin 240 which is slidably disposed inside a linear slot (or groove) 242 formed in frame 230 and the other end of scissor arm 234 supports follower wheel 124. In one embodiment, slot 242 is disposed in the spanwise direction. As pin 240 slides back and forth inside slot 242, the scissors mechanism alternately opens and closes. For example, when pin 240 moves away from pivot joint 238, the scissors mechanism closes, causing drive roller 122 and follower wheel 124 to be moved into contact with and pressed against the leading edge of the airfoil-shaped body 170, while the encoder wheel is being pressed against the trailing edge, thereby producing the gripping force. Any one of a multiplicity of known translation devices (not shown in FIG. 15) can be employed to move pin 240 along the length of slot 242, such as a motor, a piston, a solenoid, a screw drive lever, a rack and pinion assembly, or a spring.

Figure 16:
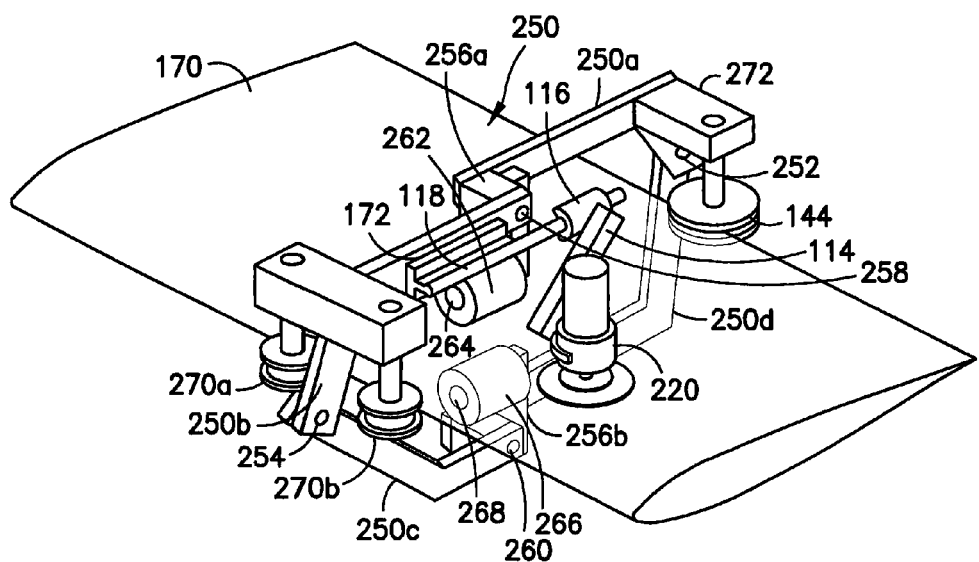
FIG. 16 is a diagram showing an isometric view of portions of a blade crawler in accordance with a further embodiment in which the crawler carries a rotary scalier and the adjustable chassis comprises a chordwise grip mechanism having a clam-shell configuration.

In accordance with another embodiment shown in FIG. 16, the chordwise grip mechanism comprises four links 250a-250d which are pivotably coupled in a clam-shell configuration to form a chassis 250. Respective first ends of links 250a and 250d are pivotably coupled by a pivot joint 252, while respective first ends of links 250b and 250c are pivotably coupled by a pivot joint 254. At the same time, respective second ends of links 250a and 250b, as well as an upper roller mounting arm 256a disposed therebetween, are all pivotably mounted to a first axle 258, while respective second ends of links 250c and 250d, as well as a lower roller mounting arm 256b disposed therebetween, are all pivotably mounted to a second axle 260. In accordance with one embodiment, a drive roller 262 is rotatably mounted on an axle 264 projecting from a distal end of the upper roller mounting arm 256a, while a flat roller 266 (not driven) is rotatably mounted on an axle 268 projecting from a distal end of the lower roller mounting arm 256b. The clam-shell chassis 250 can be configured (by rotation of links 250a-d) so that when the upper and lower roller mounting arms 256a and 256b are moved toward each other, they press drive roller 262 against the upper surface and alignment roller 266 against the lower surface of the airfoil-shaped body 170 with sufficient normal force that the resulting friction force enables the drive roller 262 to move the crawler in a spanwise direction without slippage. At the same time, a pair of alignment wheels 270a and 270b supported by link 250b and an encoder wheel 144 supported by arm 272 projecting from link 250a maintain the alignment of the crawler on the airfoil-shaped body during spanwise travel. Any one of a multiplicity of known motion devices (not shown in FIG. 16) can be employed to pinch the upper and lower halves of the chassis 250 together, such as motors, pistons, solenoids, screw drive levers, or springs.

Figure 17:
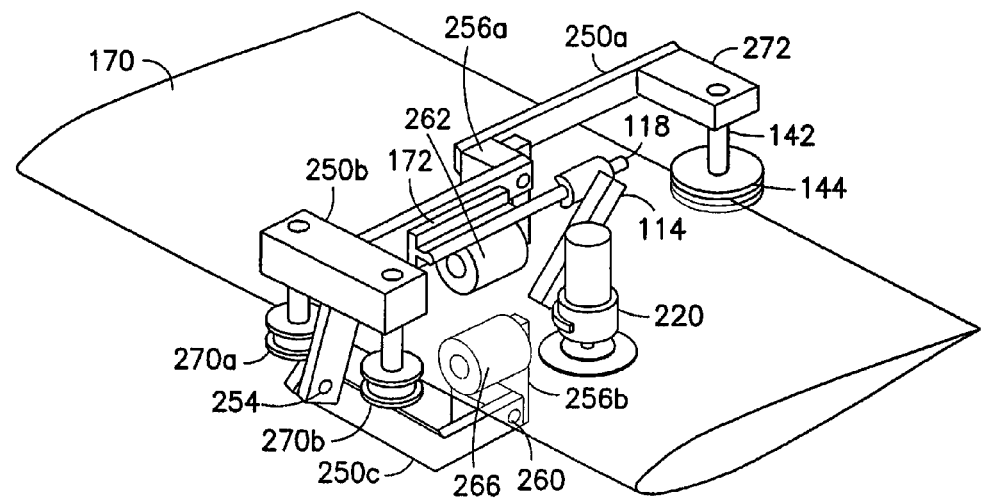
FIG. 17 is a diagram showing an isometric view of portions of a blade crawler in accordance with a variation of the embodiment depicted in FIG. 16. In this variation, the adjustable chassis comprises a chordwise grip mechanism having a clam-shell front edge configuration.

FIG. 17 is a diagram showing an isometric view of portions of a blade crawler in accordance with a variation of the embodiment depicted in FIG. 16. In this variation, the fourth link (item 250d in FIG. 16) of the adjustable chassis has been eliminated, and pivoting of the third link 250c relative to the second link 250b in either direction involves meshed gears or a controlled solenoid (not shown), which can positively urge the third link 250c in a direction that causes alignment roller 266 to press against the bottom surface of the airfoil-shaped body 170 while drive roller 262 is being urged against the top surface.

Figure 18:
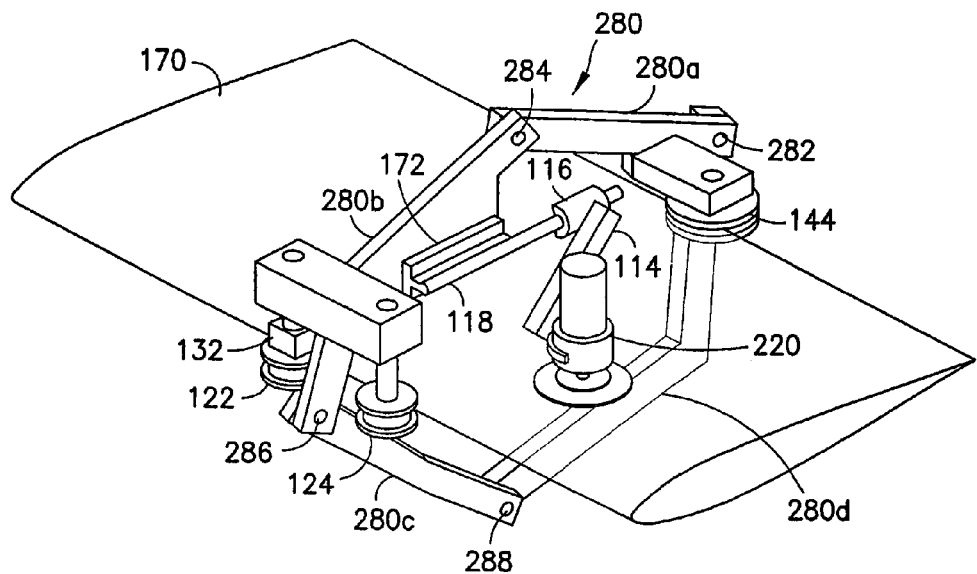
FIG. 18 is a diagram showing an isometric view of portions of a blade crawler in accordance with yet another embodiment in which the crawler carries a rotary scarfer and the adjustable chassis comprises a chordwise grip mechanism having a press configuration.

FIG. 18 shows portions of a blade crawler in accordance with yet another embodiment in which the crawler carries a rotary scarfer 220 and the adjustable chassis 280 comprises four links 280a-280d which are pivotably coupled in a press configuration. Respective first ends of links 280a and 280d are pivotably coupled by a pivot joint 282; respective first ends of links 280b and 280c are pivotably coupled by a pivot joint 286; respective second ends of links 280a and 280b are pivotably coupled by a pivot joint 284; and respective second ends of links 280c and 280d are pivotably coupled by a pivot joint 288. The press chassis 280 can be configured (by rotation of links 280a-d) so that when the pivot joints 284 and 288 are moved away from each other, the drive roller 122 and follower wheel 124 engage the leading edge while the encoder wheel 144 engages the trailing edge of the airfoil-shaped body 170. By continuing to apply a force urging the pivot joints 284 and 288 apart, the drive roller 122, follower wheel 124 and encoder wheel 144 can produce the gripping force for proper automated operation of the blade crawler. Again, any one of a multiplicity of known motion devices (not shown in FIG. 18) can be employed to press drive roller 122 and follower wheel 124 against the leading edge and encoder wheel 144 against the trailing edge, such as motors, pistons, solenoids, screw drive levers, or springs.

Position Tracking Mechanisms

In accordance with the embodiments described above, the control computer is provided with information concerning the spanwise position of the crawler. This functionality can be provided by any one of a multiplicity of known positional tracking mechanisms.

In accordance with some embodiments, an optical tracking system can be used to determine the spanwise position of the crawler. For example, U.S. Pat. No. 7,643,893 discloses a motion capture system wherein multiple motion capture cameras are set up around the object to be scanned to create a three-dimensional capture volume that captures motion for all six degrees-of-freedom of the object being tracked. The object to be tracked has a respective group of passive retro-reflective markers (at least three) attached thereto, the markers of each group being arranged in a respective unique pattern. The markers of each group are arranged in known patterns, and the information for defining the patterns is stored in a motion capture processor. Each group of markers may comprise a plurality of small spheres (e.g., about ¼ inch in diameter) attached to a rigid platform. Each motion capture camera can be a video camera of the type comprising a ring of LEDs surrounding a camera lens. In conjunction with such cameras, each retro-reflective marker may comprise a hemispherical or ball-shaped body coated with reflective paint that that reflects impinging light from the LEDs of each camera back toward the associated lens of the respective camera in a well-known manner. The motion capture system utilizes data captured from image sensors inside the cameras to triangulate the three-dimensional position of the target object between multiple cameras configured to provide overlapping projections.

Alternatively, the optical tracking mechanism may comprise a local positioning system of the type disclosed in U.S. Pat. No. 8,044,991.

In the alternative (as previously described with reference to FIG. 1), the positional tracking of the crawler's spanwise position may be provided by a rotary encoder (not shown in FIG. 1) coupled to an encoder wheel (item 144 in FIG. 1). The rotary encoder sends encoder pulses to the control computer which allow the latter to determine the spanwise coordinate of the crawler. The rotary encoder can be coupled to a follower encoder wheel or to a drive roller or drive wheel. In the alternative, a separate encoder wheel could be pivotably mounted to the crawler chassis at the end of a spring-loaded arm which urges the encoder wheel into contact with the upper surface of the airfoil-shaped body.

In accordance with other embodiments, the crawler positional tracking mechanism may comprise a light-emitting diode and a photodiode mounted to the crawler chassis in a relationship similar to what is incorporated in an optical computer mouse. This positional tracker uses an image sensor to image naturally occurring texture in the airfoil surface. Images of the surface are captured in continuous succession and compared with each other, using a process known as digital image correlation, to determine how far the crawler has moved.

In accordance with a further alternative, a capacitive linear encoder can be used to track the spanwise position of the crawler. Respective printed circuit boards of a capacitive linear encoder can be mounted on the crawler chassis and on a confronting surface of the airfoil-shaped body (the latter being removable) so that the printed circuit boards are capacitively coupled. As the crawler moves, the capacitance changes in a linear fashion and in a repeating manner. Alternatively, inductive or magnetic linear encoders can be used.

Brake System Configurations

Optionally, the blade crawlers disclosed herein may be provided with a braking system which engages the airfoil-shaped body with sufficient force to prevent movement of the crawler during the performance of NDI or a maintenance operation. This functionality can be provided by any one of a multiplicity of known brake mechanisms.

Figure 19:
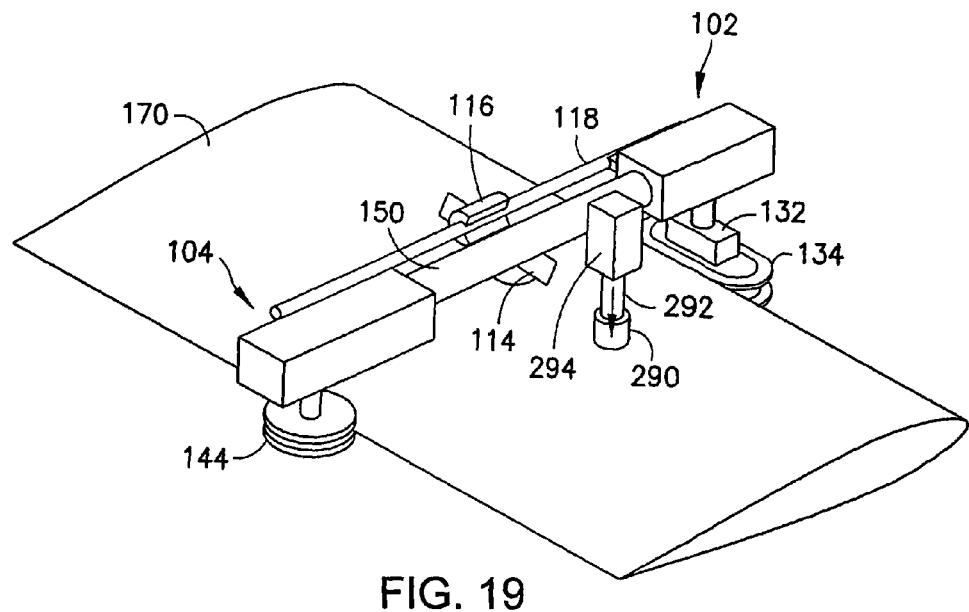
FIG. 19 is a diagram showing an isometric view (backside) of portions of a blade crawler in accordance with a further embodiment in which the chassis of the crawler carries a pressure foot brake mechanism.

In accordance with one embodiment shown in FIG. 19, the braking mechanism comprises a friction pad pressure foot 290 mounted on the end of a vertically displaceable shaft 292. The shaft 292, in turn, is operatively coupled to an actuator 294 mounted to the intercostal element 150 of a linear telescoping sleeve chordwise grip mechanism. Such a brake mechanism can be readily mounted to the various crawler chasses shown in FIGS. 14 through 18. The actuator 294 may take the form of any translation or radial motion device such as a motor, solenoid, piston, rocker mechanism, etc.

Figure 20:
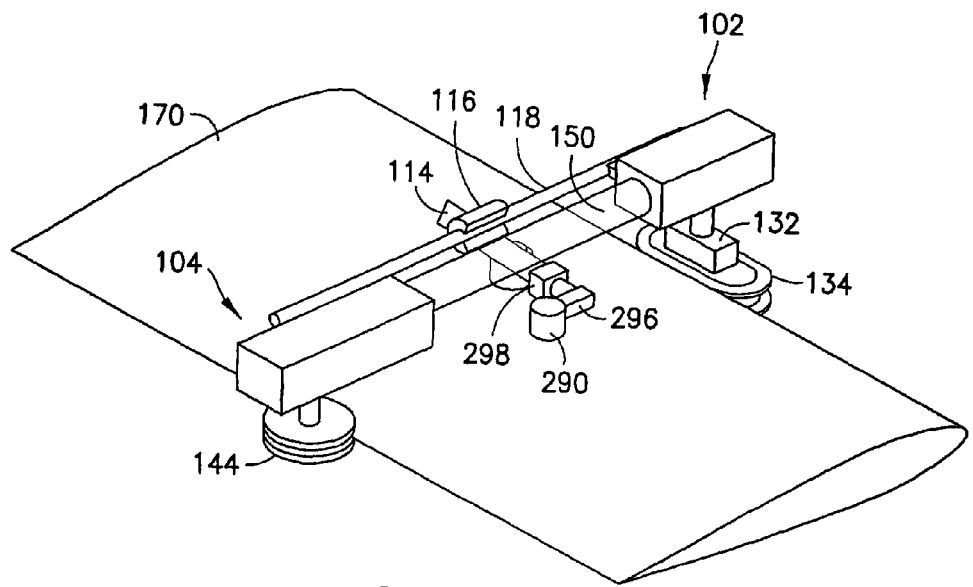
FIG. 20 is a diagram showing an isometric view (backside) of portions of a blade crawler in accordance with a further embodiment in which the end effector carries a pressure foot brake mechanism.

Alternatively, a pressure foot brake mechanism could be mounted to an end effector 220 as shown in FIG. 20. In this case, the friction pad pressure foot 290 is mounted on the end of a pivotable arm 296 connected to a radial motion device 298. Any one of a multiplicity of known radial motion devices can be employed to apply the torque on arm 296, such as a motor, a screw drive lever, a rack and pinion assembly, or a torsion spring.

In place of the friction pad pressure foot employed in the embodiments depicted in FIGS. 19 and 20, the brake mechanism may comprise a suction cup.

In accordance with alternative braking mechanisms, a brake may be incorporated in the motor which drives spanwise movement of the crawler, or a pressure pad or disc brake could be operated to engage a drive roller or alignment wheel.

Adjustable Blade Tip Stabilizing Apparatus

To facilitate the mounting and removal of the automated blade crawler disclosed herein and prevent damage to the rotorcraft blade due to the weight of the crawler, an adjustable blade tip stabilizing apparatus is provided for supporting the tip of a rotorcraft blade during inspection or maintenance. This feature enables the crawler to function on smaller or less stiff rotorcraft blades without overloading them. It also allows automated crawlers of various weights to be used on lighter, more flexible blades without harming the blades.

One embodiment of an adjustable blade tip stabilizing apparatus 10 is shown in FIGS. 21A and 21B. This apparatus is designed to support the tip of a rotorcraft blade 174, which extends radially from a root end 176, when an automated blade crawler 100 is placed on the blade. The automated blade crawler 100 is connected to an operations center (not shown) by means of cables 120 (only partly shown). The cables 120 may, for example, comprise a cable for electrical power, electrical data, and electrical control signals, and a hose supplying pressurized air or liquid.

In accordance with the embodiment shown in FIGS. 21A and 21B, the adjustable blade tip stabilizing apparatus 10 comprises a cable payout roll assembly that is mounted on and extends upward from a personnel ladder 16. The personnel ladder 16 is scaleable by the personnel assigned to the task of mounting or removing the blade crawler 100 from the blade 174.

The cable payout roll assembly comprises a free-rolling or motorized cable payout roll set 12, 14, each roll having one end rotatably coupled to a frame 24 that may be rigidly connected to the personnel ladder 16. The cable payout roll set 12, 14 enables free scanning of the automated blade crawler without dragging or binding of the cables.

The blade tip stabilizing apparatus further comprises a tip grip 20 which is mounted on the upper part 18a of a height adjustment mechanism. The lower part 18b of the height adjustment mechanism is fixedly attached to the personnel ladder 16. The upper part 18b can be moved upward or downward relative to the lower part 18a, allowing the height of the tip grip 20 to be adjusted as a function of the height of the blade tip. The tip grip 20 is designed to couple to the blade tip and provide support to prevent the latter from displacing downward under the weight of the blade crawler 100. The height of the tip grip 20 may be adjusted so that the rotorcraft blade 174 is disposed in a horizontal plane.

In accordance with one embodiment, the upper and lower parts 18a, 18b of the height adjustment mechanism may comprise mutually telescoping parts, one slidable within the other when the mechanism is manually unlocked. After the height has been adjusted, the upper part can be manually locked in place so that it cannot be moved relative to the lower part.

In accordance with an alternative embodiment, the upper and lower parts 18a, 18b of height adjustment mechanism may comprise mutually interengageable parts that are driven to displace relative to each other by a system in which at least one gear is driven to rotate by manual operation of a crank or by activation of a motor.

A laser leveler 22 (mounted to the upper portion 18a of the height adjustment mechanism) can be utilized to determine when the adjusted height of the tip grip 20 (now coupled to the blade tip) causes blade 174 to be in a horizontal position. A laser leveler is a device that can be spun to illuminate a horizontal plane with a rotating laser beam 126 (see FIG. 21A). A sensor can be placed on the root end 176 of the rotorcraft blade 174, which sensor can detect the laser beam 126 and give a signal when the sensor is in line with the beam, i.e., when the blade is horizontal.

The process steps for using the apparatus depicted in FIG. 21A are as follows:

(1) The maintainer sets up the adjustable blade tip stabilizing apparatus 10 at the tip end of an installed rotorcraft blade 174.

(2) The maintainer climbs the adjustable blade tip stabilizing apparatus 10.

(3) The stabilizer tip grip 20 is coupled to the tip of rotorcraft blade 174.

(4) The laser leveler 22 is turned on and the height of the tip grip/blade tip is adjusted using the laser line indication as a guide.

(5) The maintainer picks up and carries the automated blade crawler 100 up the steps of the personnel ladder 16.

(6) The maintainer couples the crawler 100 to the rotorcraft blade 174 at a position near the tip of the blade.

(7) The cable (or cables) 120 is inserted between the cable payout rollers 12, 14.

(8) A test scan is performed to verify the scanning movement and scanner performance for NDI or other maintenance operations.

(9) The maintainer starts the crawler 100 and dismounts from the personnel ladder 16.

(10) The automated blade crawler 100 performs its programmed function (NDI, repair, drilling, etc.) and then returns to a position near the rotorcraft blade tip.

(11) The maintainer climbs up the personnel ladder 16 and removes the crawler 100 from the blade 174.

(12) The maintainer then uncouples the tip grip 20 from the blade tip.

(13) The maintainer climbs off of the personnel ladder 16.

(14) The maintainer repeats the above steps as needed for the remaining rotorcraft blades to be maintained.

(15) The maintainer collapses the rotorcraft blade stabilizer for storage.

The blade tip stabilizing apparatus shown in FIGS. 21A and 21B solves the following problems: (a) The maintainer needs to get the crawler on and off the rotorcraft blade before and after its use. (b) Smaller or more flexible rotorcraft blades may not be able to handle the full weight of the crawler without support and/or stabilization. (c) Movement of the crawler along the rotorcraft blade may be inhibited by the power and communication cabling that goes between the crawler and the operations center.

While automated blade crawlers have been described with reference to particular embodiments, it will be understood by those skilled in the art that various changes may be made and equivalents may be substituted for elements thereof without departing from the scope of the teachings herein. In addition, many modifications may be made to adapt a particular situation to the teachings herein without departing from the essential scope thereof. Therefore it is intended that the claims set forth hereinafter not be limited to the disclosed embodiments.

As used in the claims, the term "computer system" should be construed broadly to encompass a system having at least one computer or processor, and which may have two or more interconnected computers or processors.

The invention claimed is:

1. An automated apparatus for moving an end effector over a surface of an airfoil-shaped body having leading and trailing edges, comprising:
   a chassis comprising leading and trailing edge subassemblies which are movable relative to each other to change a state of said chassis from a first state to a second state;
   a plurality of rolling elements rotatably mounted to said leading and trailing edge subassemblies, said plurality of rolling elements being situated so that said airfoil-shaped body cannot be engaged with a gripping force when said chassis is in said first state and being situated so that said airfoil-shaped body can be engaged with a gripping force when said chassis is in said second state;
   a first actuator coupled to rotate one of said plurality of rolling elements when activated;
   a support assembly coupled to and displaceable along said chassis;
   a second actuator coupled to displace said support assembly when activated;
   an end effector coupled to and carried by support assembly; and
   a third actuator coupled to actuate operation of said end effector when activated.

2. The apparatus as recited in claim 1, further comprising a fourth actuator coupled to change the state of said chassis from said first state to said second state when activated.

3. The apparatus as recited in claim 1, further comprising a control computer which is programmed to activate said first through third actuators at different times.

4. The apparatus as recited in claim 1, wherein when said chassis in said second state is being held on the airfoil-shaped body by a gripping force, activation of said first actuator causes said chassis to displace in a spanwise direction along the airfoil-shaped body.

5. The apparatus as recited in claim 4, further comprising a position tracking system mechanism which tracks the position of said chassis relative to the airfoil-shaped body by a gripping force during displacement of said chassis in a spanwise direction.

6. The apparatus as recited in claim 1, wherein when said chassis in said second state is being held on the airfoil-shaped body by a gripping force, activation of said second actuator causes said end effector to displace in a chordwise direction along the airfoil-shaped body.

7. The apparatus as recited in claim 1, further comprising a powered mechanism for changing an orientation of said end effector to achieve specific angularities.

8. The apparatus as recited in claim 1, wherein said chassis comprises a linear telescoping sleeve mechanism.

9. The apparatus as recited in claim 1, wherein said chassis comprises a frame and a pincer arm that is rotatable relative to said frame, and a distal end of said pincer arm supports one of said plurality of rolling elements.

10. The apparatus as recited in claim 1, wherein said chassis comprises a frame having a linear slot formed therein, and first and second scissor arms which are pivotably coupled to each other, wherein one end of said first scissor arm is pivotably coupled to said frame while another end of said first scissor arm supports one of said plurality of rolling elements, and one end of second scissor arm carries a pin which is slidably disposed inside said linear slot of said frame while another end of said second scissor arm supports another of said plurality of rolling elements.

11. The apparatus as recited in claim 1, wherein said chassis comprises a plurality of links pivotably coupled in a clam-shell configuration, one of said plurality of links supports one of said plurality of rolling elements, and another of said plurality of links supports another of said plurality of rolling elements.

12. The apparatus as recited in claim 1, wherein said chassis comprises a plurality of links pivotably coupled in a press configuration, one of said plurality of links supports one of said plurality of rolling elements, and another of said plurality of links supports another of said plurality of rolling elements.

13. The apparatus as recited in claim 1, further comprising a brake mechanism which is activatable for braking the apparatus when said chassis in said second state is being held on the airfoil-shaped body by a gripping force.

14. An automated apparatus for moving an end effector over a surface of an airfoil-shaped body having leading and trailing edges, comprising:
- a first support assembly comprising a forward body part, a rearward body part, and an intercostal element that interconnects said forward and rearward body parts, at least one of said forward and rearward body parts being displaceable along an axis of said intercostal element to facilitate adjustment of a distance separating said forward and rearward body parts;
- a first drive motor carried by said forward body part;
- a drive mechanism coupled to and depending from an output shaft of said drive motor and arranged to contact the airfoil-shaped body;
- a rolling element supported by said rearward body part and arranged to contact the airfoil-shaped body;
- a biasing mechanism coupled to said intercostal element and one of said forward and rearward body parts for exerting a force that urges said drive mechanism and said rolling element to grip the airfoil-shaped body;
- a guide element supported by said first support assembly;
- a second support assembly which is mounted on and displaceable along said guide element; and
- an end effector coupled to and carried by said second support assembly,
- wherein said first support assembly is displaceable in a spanwise direction along the airfoil-shaped body when said drive mechanism is driven by said drive motor, and said end effector is displaceable in a chordwise direction independent of spanwise displacement of said first support assembly.

15. The apparatus as recited in claim 14, further comprising a powered mechanism for changing an orientation of said end effector to achieve specific angularities.

* * * * *